United States Patent
McFarland et al.

(10) Patent No.: US 9,935,234 B2
(45) Date of Patent: Apr. 3, 2018

(54) METHODS FOR MANUFACTURING PHOTOELECTROSYNTHETICALLY ACTIVE HETEROSTRUCTURES

(71) Applicant: HYPERSOLAR, INC., Santa Barbara, CA (US)

(72) Inventors: Eric McFarland, Santa Barbara, CA (US); Tim Young, Santa Barbara, CA (US); Nirala Singh, Santa Barbara, CA (US); Syed Mubeen Jawahar Hussaini, Iowa City, IA (US)

(73) Assignee: HYPERSOLAR, INC., Santa Barbara, CA (US)

( * ) Notice: Subject to any disclaimer, the term of this patent is extended or adjusted under 35 U.S.C. 154(b) by 0 days.

(21) Appl. No.: 15/418,236

(22) Filed: Jan. 27, 2017

(65) Prior Publication Data
US 2017/0141258 A1   May 18, 2017

Related U.S. Application Data

(62) Division of application No. 13/676,901, filed on Nov. 14, 2012, now Pat. No. 9,593,053.

(60) Provisional application No. 61/559,717, filed on Nov. 14, 2011.

(51) Int. Cl.
| | |
|---|---|
| *H01L 31/18* | (2006.01) |
| *C25D 7/12* | (2006.01) |
| *C23C 14/24* | (2006.01) |
| *C23C 14/58* | (2006.01) |
| *C23C 16/455* | (2006.01) |

(Continued)

(52) U.S. Cl.
CPC ............ *H01L 31/186* (2013.01); *C23C 14/24* (2013.01); *C23C 14/5873* (2013.01); *C23C 16/45525* (2013.01); *C25D 7/126* (2013.01); *H01L 31/0236* (2013.01); *H01L 31/108* (2013.01)

(58) Field of Classification Search
CPC ........... H01L 31/022466; H01L 31/184; C07C 1/0495; C25B 1/003
See application file for complete search history.

(56) References Cited

U.S. PATENT DOCUMENTS

2007/0259217 A1* 11/2007 Logan ................ H01M 4/90
                                                                   429/2
2009/0212275 A1*  8/2009 Park .................. H01L 51/0587
                                                                   257/9

(Continued)

*Primary Examiner* — Stephen Bradley
(74) *Attorney, Agent, or Firm* — Workman Nydegger

(57) ABSTRACT

A photoelectrosynthetically active heterostructure (PAH) is manufactured by forming or providing cavities in an electrically insulating material; forming or providing an electrically conductive layer on a side of the electrically insulating material; depositing an electrocatalyst cathode layer in the cavities; depositing one or more layers of light-absorbing semiconductor material in the cavities; depositing an electrocatalyst anode layer in the cavities; removing the layer of electrically conductive metal; and forming a hydrogen permeable layer over the electrocatalyst cathode layer. The one or more layers of light-absorbing semiconductor material can form a p-n junction or Schottky junction. The PAH can be used in photoelectrosynthetic processes to produce desired products, such as reduction product (e.g., methane gas, methanol, or carbon monoxide) from carbon dioxide and liquid waste streams.

18 Claims, 28 Drawing Sheets

(51) Int. Cl.
*H01L 31/108* (2006.01)
*H01L 31/0236* (2006.01)

(56) References Cited

U.S. PATENT DOCUMENTS

2010/0133111 A1* 6/2010 Nocera .............. H01M 14/005
 205/633
2010/0269894 A1* 10/2010 Misra .................... B82Y 20/00
 136/252
2011/0129742 A1* 6/2011 Karpov .................. H01M 4/92
 429/414

* cited by examiner

METHODS FOR MANUFACTURING PHOTOELECTROSYNTHETICALLY ACTIVE HETEROSTRUCTURES

CROSS-REFERENCE TO RELATED APPLICATION

This application is a division of U.S. patent application Ser. No. 13/676,901, filed Nov. 14, 2012, which claims the benefit of U.S. Provisional Patent Application No. 61/559,717, filed Nov. 14, 2011, the disclosures of which are incorporated herein in its entirety.

BACKGROUND OF THE INVENTION

1. Field of the Invention

The invention is in the field of micro-scale photovoltaic devices, more particularly photoelectrochemical/photoelectrosynthetic devices, processes and systems for utilizing solar energy to drive chemical reactions.

2. Review of Technology

There is great interest in renewable energy generation in order to replace conventional fossil fuels. This includes utilizing solar, wind and biomass for producing fuels. Solar energy is particularly interesting because it is a fundamental renewable energy source that can be used to continuously, noiselessly, and passively generate fuels once an infrastructure for fuel production has been developed. Photovoltaic devices consist of semiconductor materials that are capable of capturing photons from solar irradiation and converting them into electrical energy (i.e., a current having an electrical potential).

Solar cells are effectively used to provide power for satellites in space operations and stand alone appliances that are not connected to the electrical grid. However, connecting solar cells to a grid is far more complicated because the direct current power produced by solar cells must be converted to AC power according to the power transmission system into which they are to be integrated. Moreover, solar cells require complex and relatively expensive wiring to interconnect a system of solar cells together to provide electrical power to be input into the grid. Corrosion, heat stress and internal short-circuits can reduce or eliminate the ability of a solar cell to generate power. In the case of solar panels, failure of a subsection may cause catastrophic and irreparable failure and require replacement of the entire panel.

Solar energy can also be used in photoelectrosynthetic processes to produce desired products through photo-oxidation and photo-reduction of chemical components in a feedstock. For example, U.S. Pat. No. 4,263,110 to Meyerand et al. discloses the use of semiconductor "platelets" suspended in a reactor vessel containing aqueous hydrobromic acid to produce hydrogen gas and bromine as products (see FIGS. 1A and 1E of this disclosure). The semiconductor "platelet" 100 shown in FIG. 1A includes an n-doped semiconductor material 101 and a p-doped semiconductor material 102. An edgewise insulation material 103 (e.g., conventional epoxy resin) is shown broken away to expose ohmic contacts 104.

U.S. Pat. No. 4,094,751 to Nozik discloses Schottky-type and p-n junction type photochemical diodes. As shown in FIG. 1B, a cross-section of an exemplary Schottky diode 110 is shown suspended in a reaction matrix 118 of a reactor 111 and includes an appropriately doped semiconductor 112 (n- or p-type), an ohmic contact 113 adjacent to the semiconductor, and a metallic contact or layer 114 adjacent to the ohmic contact 113. The Schottky diode 110 further includes a semiconductor/matrix interface 115 and a metal/matrix interface 117. Absorption of light energy 116 by the semiconductor layer 112 creates electrons and holes (not shown). For n-type semiconductors, electrons move across the ohmic contact 113 to the metallic layer 114, where they are injected through the metal/matrix interface 117 into the reactant matrix 118 to drive a reduction reaction (such as $H_2$ evolution). Holes are injected through the semiconductor/matrix interface 115 into the reactant matrix to promote an oxidation reaction (such as the formation of $O_2$ or $H_2O_2$). The charge flows are reversed for p-type semiconductors.

FIGS. 1C and 1D show exemplary p-n junction type photochemical diodes disclosed in Nozik. As shown in cross-section in FIG. 1C, an exemplary side-by-side p-n junction type photochemical diode 120 is configured to absorb incident light 121 on one side and includes a p-type semiconductor 123, which is provided with an ohmic contact 124, and an n-type semiconductor 125, which is provided with an ohmic contact 126. The two ohmic contacts 124, 126 are optionally connected through a metal contact 127, which serves to act as a support for the side-by-side diode 120, which is shown suspended in reaction matrix 128.

As alternatively shown in cross-section in FIG. 1D, an exemplary stacked p-n junction type photochemical diode 130 is configured to absorb incident light 131 on both sides and includes a p-type semiconductor 133, which is provided with an ohmic contact 134, and an n-type semiconductor 135, which is provided with an ohmic contact 136. The two ohmic contacts 134, 136 are shown connected through an optional metal contact 137.

FIG. 1E illustrates an exemplary apparatus 140 for producing hydrogen and bromine from hydrobromic acid, as disclosed in Meyerand et al. Apparatus 140 includes platelet particles 141, a hydrobromic acid electrolyte solution 144 flowing as indicated by arrows 145. The flow of the electrolyte solution 144 can be such that the platelet particles 141 remain substantially suspended between the area defined by lower and upper screens 146a, 146b. Lower screen 146a primarily provides a resting place for the platelets 141 during shutdown, while lower screen 146a and upper screen 146b confine errant platelets 141 during positive and negative flow surges and turbulence. Screens 146a, 146b can be optionally removed once system stability is attained. Radiant energy 143 drives the formation of bromine 147, which settles to the bottom of the apparatus, and hydrogen gas 149, which bubbles to the surface and is expelled through port 148. The hydrobromic acid electrolyte solution 144 can be run through a monitoring station 150 and additional electrolyte added as needed.

Notwithstanding the foregoing, commercially feasible production of hydrogen, bromine and other products using semiconductor powered devices remains elusive and no commercial system for producing chemicals of any kind using artificial solar photoelectrosynthesis has ever been demonstrated. Accordingly, there remains a need to find commercially and technically feasible ways to utilize solar energy to drive useful chemical reactions. There is also a need to produce hydrocarbon fuels from renewable energy sources such as solar energy. There is also an ongoing need to remove or sequester carbon dioxide from the atmosphere.

BRIEF SUMMARY OF THE INVENTION

Disclosed herein are methods for producing desired chemical products, including hydrocarbons such as methane and other alkanes, synthesis gas (carbon monoxide and hydrogen), and methanol, from carbon dioxide and oxidizable reactant compounds in wastewater as a feedstock using solar energy to drive at least a portion of the chemical reaction process (e.g., to produce hydrogen gas). Photoelectrosynthetic processes employ photoelectrosynthetically active heterostructures (PAHs) to absorb sunlight and transform the light energy into electrochemical potential energy, which converts reactants containing hydrogen atoms into products, which react with carbon dioxide to form desired chemical products. Also disclosed are photoelectrosynthetic and thermochemical reaction systems used to produce methane gas from a hydrogen containing source, PAHs, solar energy, and carbon dioxide, as well as improved PAHs having increased stability and efficiency and methods of making such PAHs.

The methods and systems may employ photoelectrosynthetically active heterostructures (PAHs) that are similar to those known in the art or improved PAHs disclosed herein which have improved stability, energy conversion efficiency, and/or other desired attributes or characteristics. The improved PAHs can be manufactured using novel methods as disclosed herein and contain novel structures and components.

In the first step of an exemplary two-step photoelectrosynthetic and thermochemical process, molecular hydrogen is photoelectrosynthetically produced by contacting a feed stream containing molecules having hydrogen atoms with PAHs in the presence of sunlight. Light energy is used to drive the reduction half reaction in which hydrogen ions and/or water molecules in the aqueous solution are reduced at the cathodes of the PAHs to form hydrogen gas. In a parallel half reaction, anions in the solution are oxidized at the anodes of the PAHs to form oxidized co-product(s). In a second step, hydrogen gas produced in the first step is reacted with carbon dioxide in the presence of a thermal catalyst under appropriate reaction conditions to form a desired reduction product of carbon dioxide as the primary product (e.g., methane in an exothermic reaction with water as a co-product).

An exemplary photoelectrosynthetic system includes a photoelectrosynthetic reactor vessel containing a hydrogen source and PAHs. The vessel includes a light permeable outer wall that allows sunlight to enter the vessel and interact with at least some of the PAHs in the vessel to produce an electric potential between the cathodes and anodes of the PAHs. The hydrogen source (e.g., waste stream containing carbohydrates or acids, or electron donor reagents ($SO_3^{2-}$ for example)) provides protons that interact with PAHs energized by solar energy to produce hydrogen at the cathodes of PAHs, which is collected in the vessel. Protons from the hydrogen source can be carried to the PAH cathodes by hydronium ions ($H_3O^+$) in an acidic reaction environment or water ($H_2O$) in a basic reaction environment. Molecules from the hydrogen source are oxidized at the anodes of PAHs to generate co-product(s). The exemplary system further includes a reaction chamber or region in, attached to, or separate from the photoelectrosynthetic reaction vessel in which the hydrogen produced in the first reaction is reacted with carbon dioxide in the presence of a catalyst as an exothermic process to form methane, which is collected for use or storage, or other reduction products of carbon dioxide so as to form, e.g., synthesis gas, methanol, formaldehyde or formic acid.

Exemplary PAHs that may be used in connection with the disclosed methods and systems to photoelectrosynthetically produce hydrogen include one or more layers of light absorbing p-type and/or n-type semiconductor material, an interface material between specific areas of the semiconductor and an anode material, an anode material, an interface material between other areas of the semiconductor and a cathode material, a cathode material, an interface material between other areas of the semiconductor and a protective coating, a protective coating on the semiconductor material, and a hydrogen permeable coating on the cathode. The semiconductor material system(s) can consist of a p-n junction, a Schottky barrier to form a Schottky junction, and/or be attached to molecular absorbers.

The PAHs can be single- or multi-cell structures (e.g., to increase electrical potentials between the cathode and anode). They can be arranged on or otherwise attached to a substrate or suspended in a reaction solution as individual particles (e.g., nanoparticles).

Exemplary methods for manufacturing PAHs include forming a semiconductor material as a particle or within a well or pore of a substrate, forming interface layers on the semiconductor material, forming an anode on the interface layer adjacent to the p-type semiconductor material, forming a cathode on the interface layer adjacent to the n-type semiconductor material, forming a protective coating on exposed surfaces of the semiconductor material, and forming a hydrogen permeable coating on the cathode. The foregoing steps are not necessarily performed in any particular order but rather according to the specific type of PAH being manufactured and the reaction sequences being employed. In the case of Schottky junctions, the semiconductor material may be only one of a p-type or n-type material and wherein one of the metal electrode layers can function as a Schottky barrier. Molecular absorbers may be used alone or attached to a p-type or n-type semiconductor material and rely on ballistic charge transfer across the semiconductor material to create an electrical potential.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

I. Introduction

Photoelectrosynthetic processes are disclosed for producing hydrogen gas from organic waste streams or other sources of hydrogen involving the use of photoelectrosynthetically active heterostructures (PAHs) and sunlight. Hydrogen produced via one or more photoelectrosynthetic processes is then reacted with carbon dioxide via a thermochemical process to produce carbon-containing reduced products, including methane and other alkanes, methanol, and carbon monoxide. The two step processes involving a photoelectrosynthetic reaction system and a thermochemical process used to produce methane gas or other reduction products of carbon dioxide using the disclosed processes are also disclosed. The methods and systems may employ PAHs known in the art or improved PAHs having improved stability, energy conversion activity, and/or other desired attributes as disclosed herein.

The methods and apparatus disclosed herein solve needs relating to efficient solar energy conversion, which include systems which remain stable over time and are relative inexpensive compared to other technologies. Efficiency can be promoted by providing methods and systems that are able to absorb a wider range of the solar spectrum, efficiently convert the absorbed solar irradiation energy into useful fuels, and separate and store such fuels for later use. Capital costs are reduced by eliminating external circuitry as compared to an electrolytic system that consists of photovoltaic cells and electrolyzer cells used to produce hydrogen. Capital costs are also reduced by using inexpensive and earth abundant materials in the disclosed photoelectrosynthetic process. In addition, deactivation of a subset of PAHs in a photoelectrosynthetic system does not affect the ability of the remaining PAHs to drive the desired photoelectrosynthetic reactions.

Figure 1A:
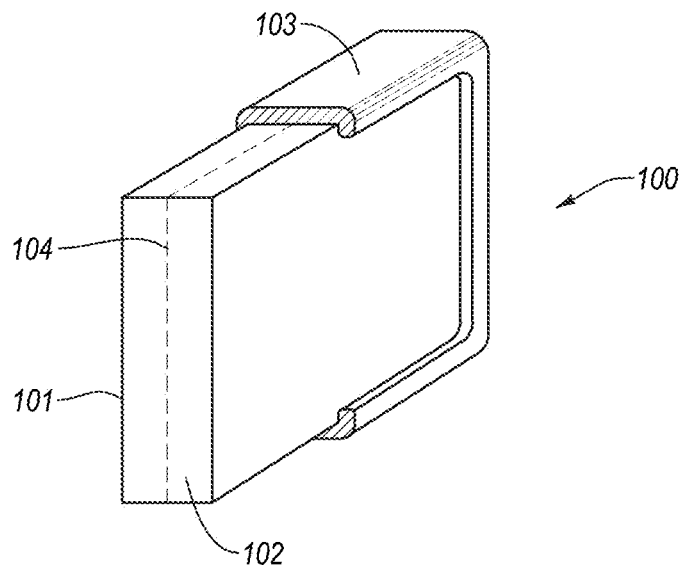
FIG. 1A is a schematic perspective view of a prior art photoelectrosynthetic "platelet" used to convert light energy into electrochemical energy.
Figure 1B:
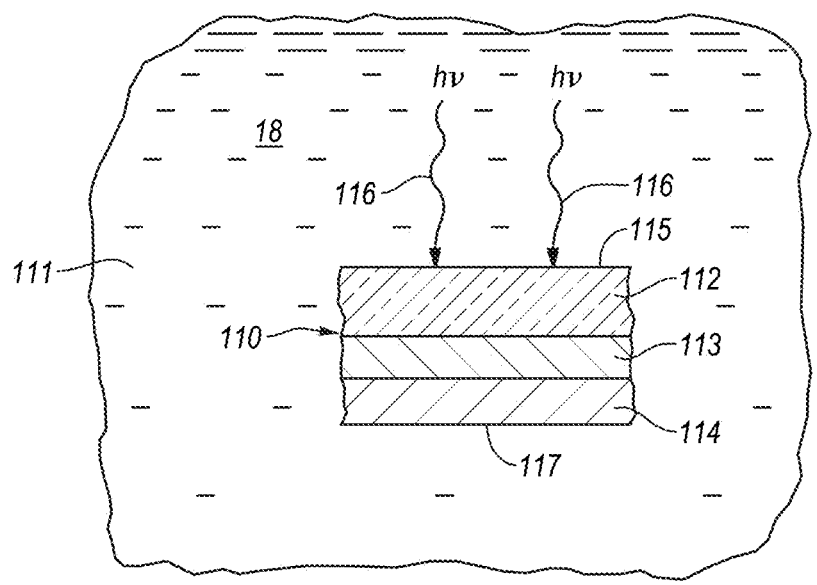
FIG. 1B is a schematic cross-section view of a prior art Schottky-type photoelectrosynthetic diode used to convert light energy into electrochemical energy.
Figure 1C:
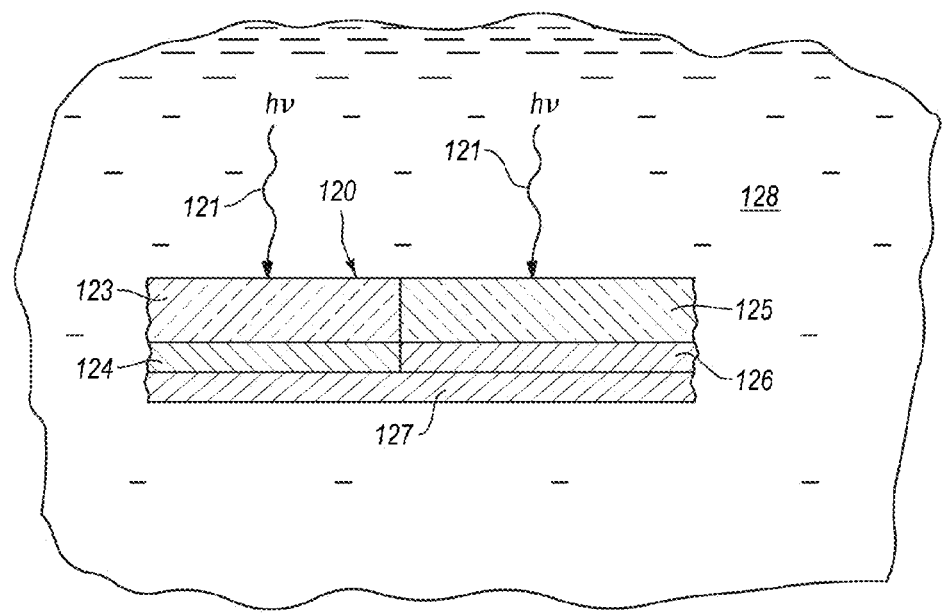
FIG. 1C is a schematic cross-section view of a prior art p-n type photoelectrosynthetic diode having a side-by-side configuration used to convert light energy into electrochemical energy.
Figure 1D:
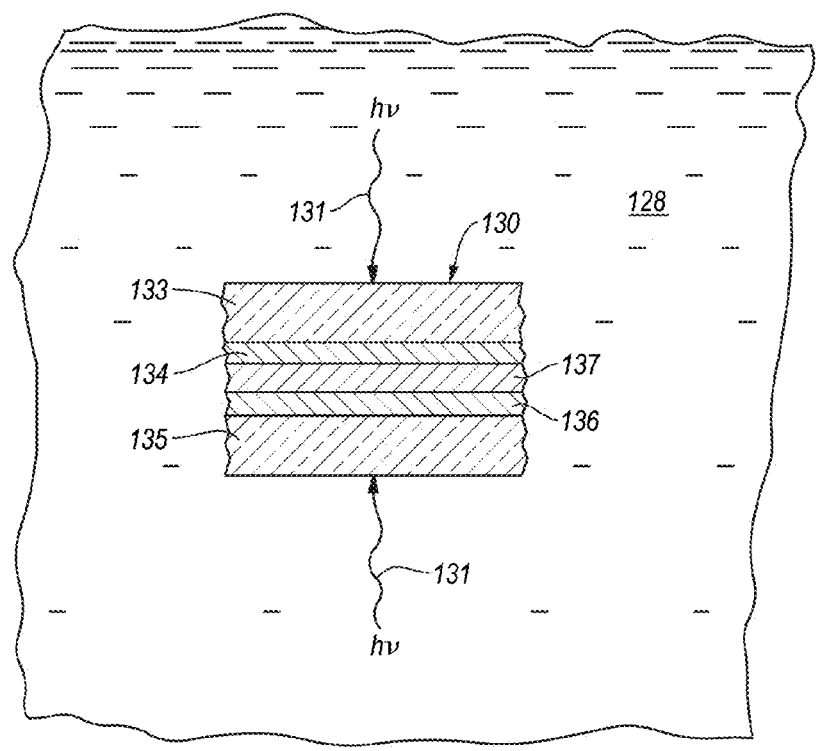
FIG. 1D is a schematic cross-section view of a prior art p-n type photoelectrosynthetic diode having a stacked configuration used to convert light energy into electrochemical energy.
Figure 1E:
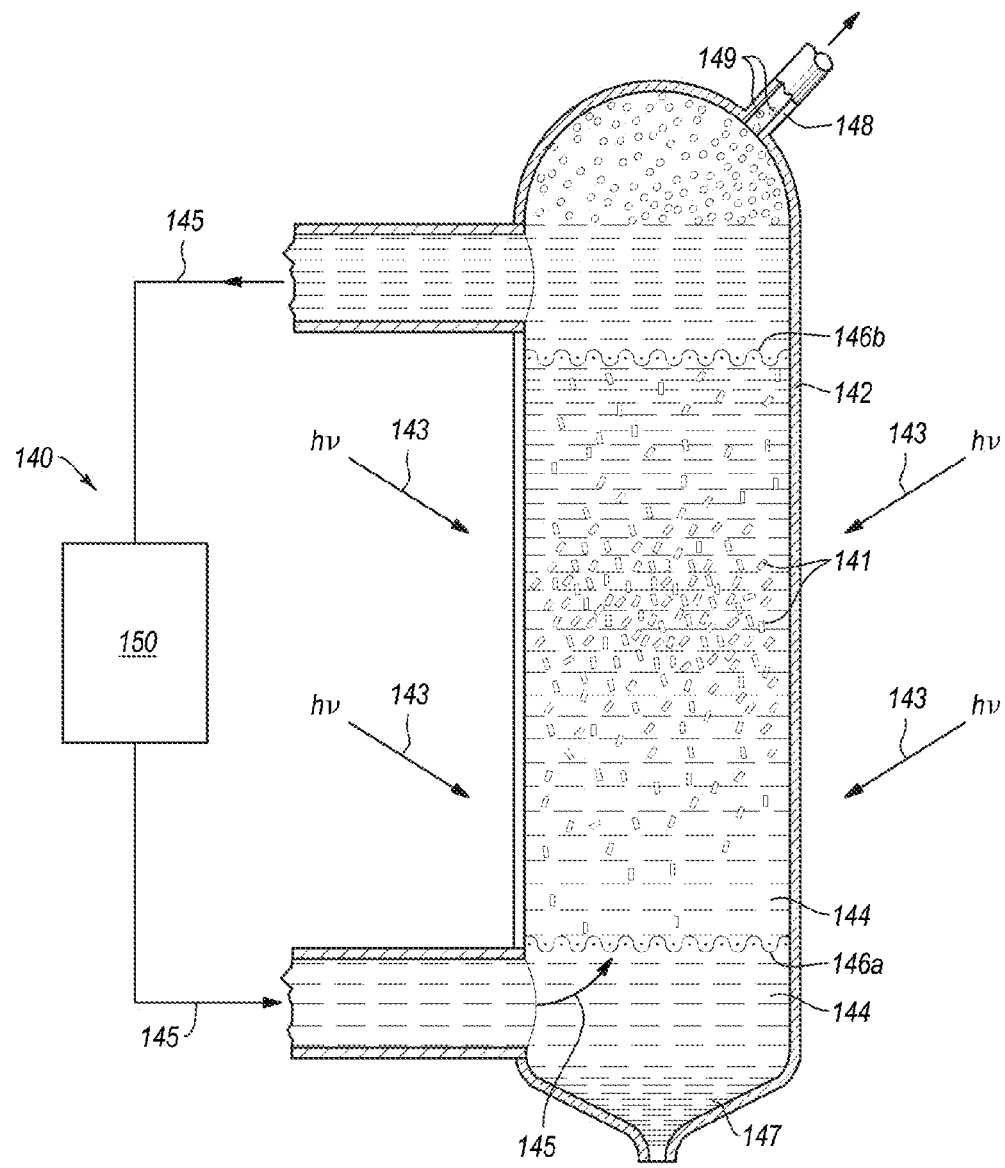
FIG. 1E is a schematic cross-section view of a prior art apparatus used to produce hydrogen gas and bromine liquid from a feed stream containing aqueous hydrobromic acid.
Figure 2A:
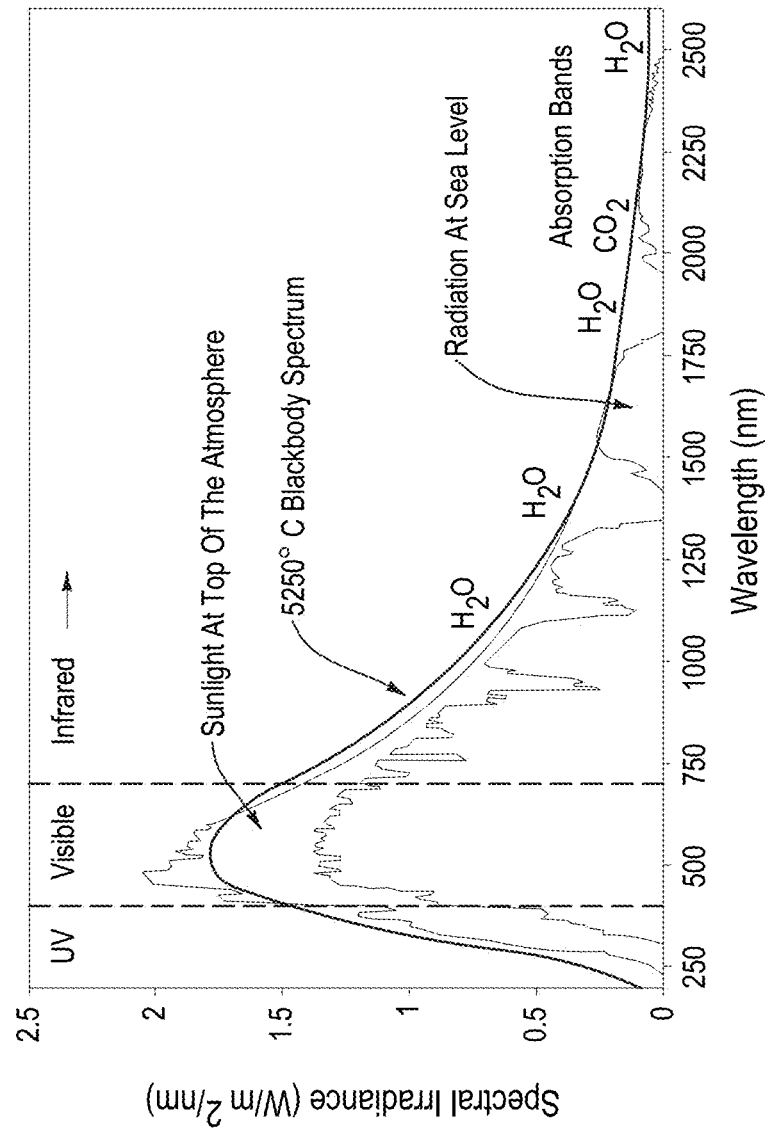
FIG. 2A is chart that schematically illustrates the spectral irradiance of sunlight as a function of wavelength.

The solar energy conversion efficiency depends, in part, on the semiconductor bandgap within the PAHs used to drive the photoelectrosynthetic processes utilized herein. To illustrate this point, reference is made to FIGS. 2A and 2B. FIG. 2A depicts a solar radiation spectrum that compares spectral irradiance (W/m²/nm) as a function of wavelength (nm). The jagged curve with the highest peaks depicts the solar radiation spectrum at the top of the atmosphere. The jagged curve with the lowest peaks depicts the solar radiation spectrum at sea level. The smooth, bold curve depicts a blackbody spectrum at 5250° C. The spectral irradiance at sea level dips precipitously at wavelengths corresponding to absorption bands of water.

The ability of a PAH to absorb a particular wavelength depends on its bandgap, which defines the potential of the electrons excited within the PAH. A semiconductor can only absorb photons with wavelengths corresponding to energies that equal or exceed its bandgap energy. Thus, the smaller the bandgap, the greater is the range of photon wavelengths that can be absorbed by the PAH and the more photons are absorbed to excite electrons. On the other hand, the bandgap is related to the electrochemical potential (voltage) the PAH can produce, and with higher voltages available, thermodynamically there are a greater number of electrochemical reactions that can be performed. Thus, the smaller the bandgap, the smaller is the electrical potential of the electrons generated by the PAH and the fewer are the types of reactions that can be powered by the PAH.

Figure 2B:
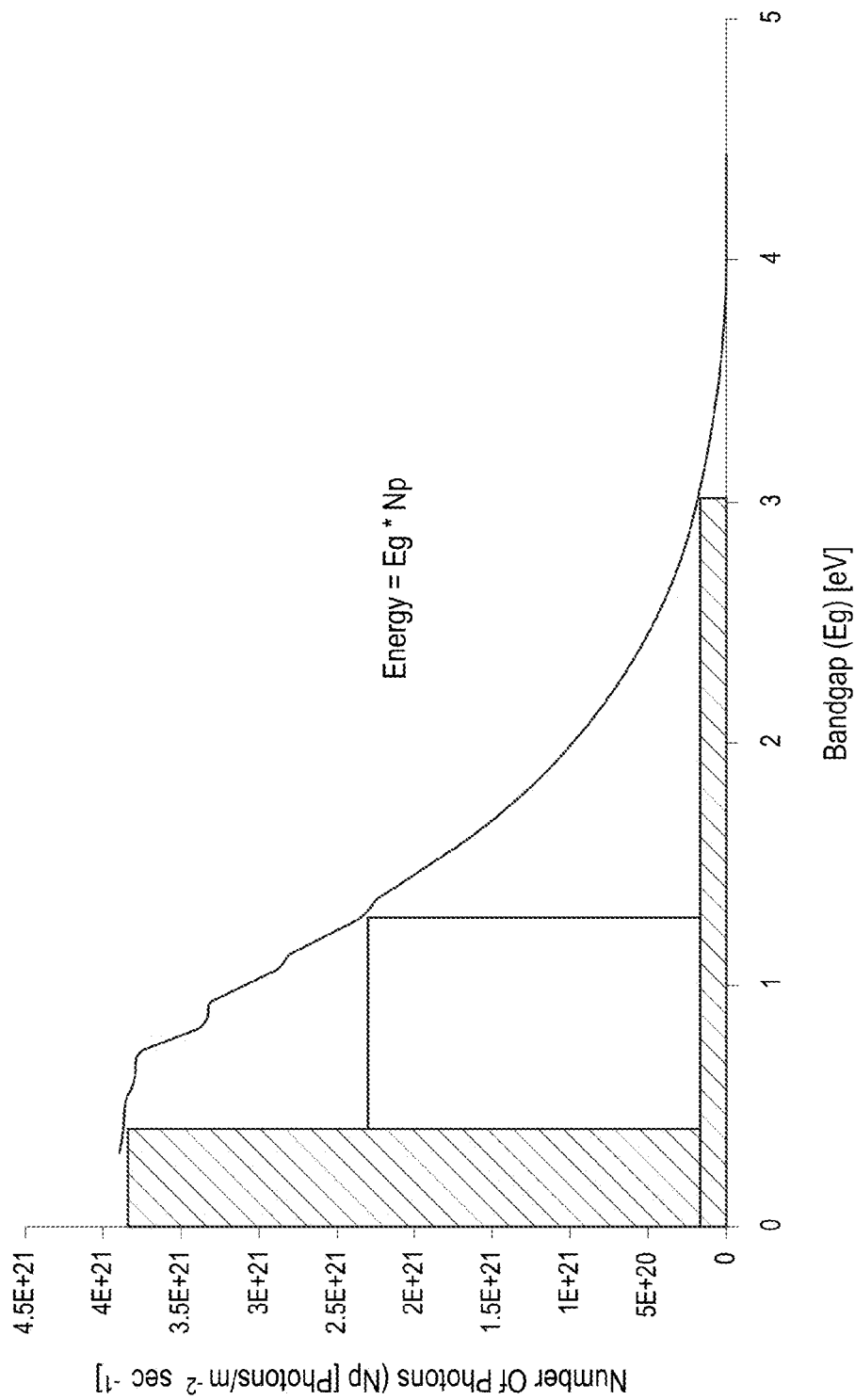
FIG. 2B is chart that schematically illustrates the relationship between the number of light photons in sunlight that are available for conversion into electrochemical energy as a function of semiconductor bandgap(s)

The importance of balancing the amount of light absorbed by the semiconductor with semiconductor bandgap is illustrated in FIG. 2B. The total power produced by a PAH can be expressed as Power=Np*Eg, where Np is the number of photons of sunlight absorbed by the PAH per second and Eg is its bandgap energy. The large rectangular area in FIG. 2B represents a good balance between the rate of photons absorbed and energy of created electron-hole pairs. The narrow rectangular area on the top of the chart represents semiconductors that absorb more photons with excessively low bandgap energy. The result is that the total useful energy generated by photons is low. The narrow rectangular area on the bottom of the chart represents semiconductors that have high bandgap but absorb much less number of photons. Again, the result is low total useful energy. It can therefore be advantageous to select PAHs that are able to absorb a sufficient number of photons while having sufficiently high bandgap energy to provide an optimal electrical energy level per photon.

In addition to being able to drive useful redox reactions, the PAH may itself undesirably react with substances in the reaction chamber. This can cause corrosion and deactivation of the semiconductor device. For example, oxidation can convert silicon-containing semiconductor materials to silicon dioxide. Conversely, semiconductor compounds like cadmium sulfide (CdS) can be reduced to cadmium metal (Cd). The tendency to undergo photo corrosion is especially prevalent in the case of low bandgap energy semiconductor devices, which limits their usefulness in many reactions. It is therefore important to protect the semiconductor devices to promote longevity. The inability to avoid deactivation may explain why semiconductor devices known in the art have not been used in commercially viable process for producing useful fuels. Improved semiconductor devices that are better able to resist corrosion and remain active over longer periods of use are described more fully below.

II. Producing Desired Products from Hydrogen Source and $CO_2$

Figure 3:
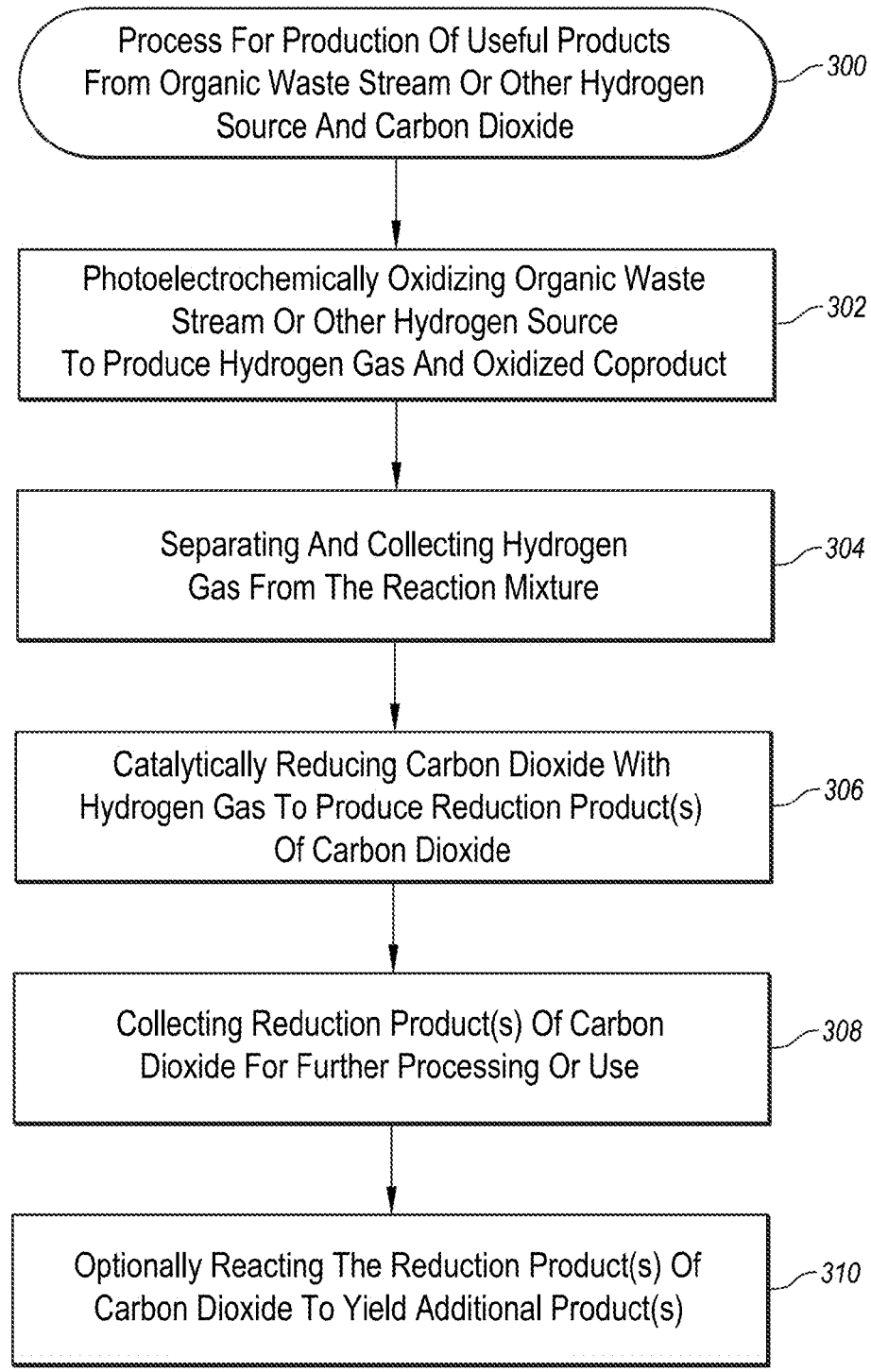
FIG. 3 is a flow diagram of an exemplary process for the production of methane from an organic waste stream and carbon dioxide.
Figure 4:
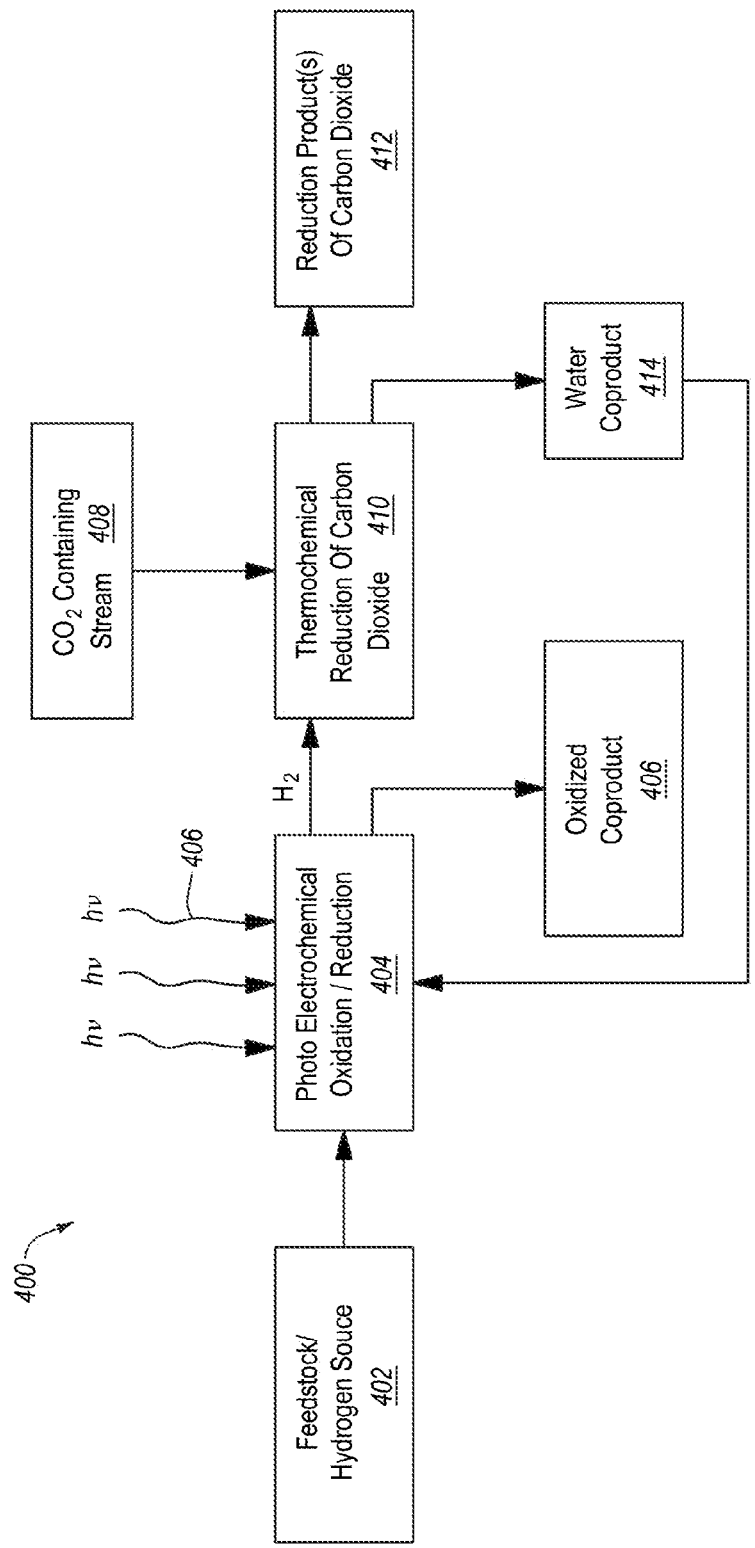
FIG. 4 schematically depicts an exemplary reaction system for the photoelectrosynthetic production of hydrogen from a feedstock that includes a hydrogen source and subsequent reaction of hydrogen with carbon dioxide to form methane.

FIGS. 3 and 4 illustrate exemplary methods and systems for producing desired products in a two-step process from a hydrogen source using PAHs to first absorb solar energy and produce hydrogen gas from the hydrogen source followed by the reduction of carbon dioxide using the hydrogen gas to yield desired reduction products. Examples of desired reduction products include, but are not limited to, methane, methanol, formaldehyde, and synthesis gas, which can be used in Fischer-Tropsch processes to make liquid fuels, diesel and/or paraffins.

FIG. 3 is a flow chart that depicts the basic steps of an embodiment for an exemplary process 300 for producing methane from an organic waste stream or other hydrogen source. A first step 302 involves photochemically oxidizing an organic waste stream or other hydrogen source to produce hydrogen gas and an oxidized co-product. For example, light energy is converted by PAHs in a reaction vessel into electrical energy having sufficient voltage to drive a redox reaction involving the hydrogen source. Light energy is converted using semiconductor devices known in the art and/or photoelectrosynthetically active heterostructures (PAHs) disclosed hereinafter, which can be dispersed as a suspension within the reaction vessel, packed as fixed bed, or attached to a floor or fixed surface in the reactor.

According to one embodiment, the half reaction in which hydrogen containing ions or molecules are reduced to hydrogen gas are provided by water molecules in either an acidic or basic environment. Production of the oxidized co-product in the other half reaction releases hydrogen ions that go into solution and recombine with water molecules to form hydronium ions ($H_3O^+$) in an acidic environment or water ($H_2O$) in a basic environment.

A second step 304 involves separating and collecting hydrogen gas from the reaction mixture. Because the reaction mixture will typically be a liquid or liquid-solid slurry and hydrogen has low solubility in aqueous solutions, the hydrogen will form bubbles and rise to the surface of the reaction mixture or otherwise leave the liquid phase and collect as a relatively higher purity gas at the top of the reactor. From here, the hydrogen gas can either be utilized (reacted) within the reactor gas space or be drawn off and utilized in a separate downstream reactor to form reduction products of carbon dioxide.

A third step 306 involves catalytically reacting hydrogen gas produced in step 2 and collected in step 304 with carbon dioxide to form desired reduction products of carbon dioxide. Specific catalysts and conditions can reduce the carbon dioxide with varying amounts of hydrogen to produce several produces including but not limited to carbon monoxide and water, formic acid and water, methanol and water, or methane and water. The last three reactions are exothermic and generally have high conversions of carbon dioxide, whereas the first (reverse water-gas shift reaction) is only minimally endothermic (+41 kJ/mole) and in excess hydrogen will proceed to high carbon dioxide conversions at modest temperature. Additional hydrogen can be added to the carbon monoxide in order to product synthesis gas having a desired $H_2$/CO ratio.

The carbon dioxide can be provided in a wide range of concentrations from various sources, discussed more fully below. Because hydrogen production using light energy is itself a relatively slow process, the kinetics of reacting hydrogen at modest temperatures produced by the method with carbon dioxide can be similarly slow. This permits the reduction of carbon dioxide to be carried out at relatively low temperature and pressure, including within the head space of the reaction vessel used to photoelectrosynthetically produce hydrogen. Alternatively, hydrogen can be drawn off and sent to a downstream reactor to produce methane or other reduction product(s) of carbon dioxide. Moreover because hydrogen production relies on light energy, while the conversion of hydrogen and carbon dioxide into methane or other product(s) does not, the kinetics of the reaction used to produce methane or other product(s) can actually be slower than the rate at which hydrogen is produced. For example, hydrogen that builds up more quickly during daylight hours can be used up during night time to produce desired reduction product(s) of carbon dioxide. Water produced as a co-product can be condensed within the vessel where methane is produced and returned to the solution, or else it can be channeled back into the reaction vessel from a downstream reactor used to produce methane or other reduction product(s).

A fourth step 308 involves collecting the methane or other product(s) product for further processing or use. The methane gas or other product(s) will typically be removed from the reactor as it is produced in order to further drive the reaction forward according to the Le Chatelier principle. According to one embodiment, the head space in the photoreactor can be completely purged with carbon dioxide at dawn after methane or other product(s) are formed during the night and just before production of hydrogen resumes with the rising of the sun. The methane or other product(s) produced in step 308 may contain impurities and therefore require cleaning processes to remove such impurities.

An optional fifth step 310 involves reacting the reduction product(s) of carbon dioxide and hydrogen to yield additional product(s). For example, synthesis gas can be utilized in one or more Fischer-Tropsch processes to form one or more liquid hydrocarbon fuels, including, but not limited to, diesel, naphtha, or other paraffins.

FIG. 4 illustrates an exemplary system 400 for producing methane from a hydrogen source, sunlight and a carbon dioxide stream. A feedstock 402 provides a source of hydrogen that can be photoelectrosynthetically converted into hydrogen gas using PAHs or other semiconductor light absorbers capable of converting light energy into electrical energy. The feedstock can be one or more of a number of different waste streams, including, but not limited to, waste streams from complex organic chemical industries (e.g., pharmaceutical processing, pesticide manufacturing, hydrocarbon refining, detergents, plastics, pulp and paper mills, textile dyes), agricultural, biofuels, chemical manufacturing (e.g., toxic hydrogen sulfide, hydrogen bromide, hydrogen chloride), municipal wastewater, iron and steel industry, coal plants, and tannery.

In general, the feedstock 402 includes water with some sort of supporting electrolyte to provide conductivity. The waste stream may include organic or inorganic molecules such as, but not limited to, one or more of celluloses, hydrocarbons, non-biocompatible pollutants, alcohols, ethanol, methanol, isopropyl alcohol, pesticides, glucose, phenols, carboxylic acids, mineral acids, cyanide, ammonia, acetic acid, dyes, surfactants, chlorophenols, anilines, oxalic acid, and tartaric acid.

The feedstock 402 is introduced into a reaction vessel 404 together with PAHs or other semiconductor light absorbers capable of converting light energy into electrical energy. The reaction vessel 404 will generally have transparent walls that permit light radiation 406 from the sun to penetrate into the reaction mixture, where it can be converted into electrical energy by the PAHs or other semiconductor light absorbers in order to drive oxidation and reduction reactions.

According to one embodiment, the reaction vessel 404 may comprise a flexible polymer wall or chamber that is placed over a relatively large surface area and that has a low height compared to the length and width of the vessel 404 in order to maximize the amount of incident light that comes into contact with the reaction mixture and PAHs. A conduit introduces the feedstock 402 at one end, which is allowed or caused to slowly flow through the vessel 404 and then be removed from the other side. The rate at which the feedstock passes 402 through the vessel can be a function of the rate at which the hydrogen containing molecules are converted into hydrogen and oxidized co-product(s) 406. Thus, the feedstock may pass through the reaction vessel 404 during the day but not during the night when there is no sunlight to drive the reaction. Moreover, the kinetics of hydrogen production may itself change depending on such things as the angle and/or intensity of incident sunlight, the amount of cloud cover, the temperature of the reaction mixture, the opacity or transparency of the reaction mixture, and the like.

The reduced hydrogen product can be collected from or within the reaction vessel 404. In one embodiment, the hydrogen gas rises to the top of the reaction mixture and collects in the head space of the reaction vessel 404. The oxidized co-product(s) 406 can be drawn off from the reaction vessel 404 together with the spent feedstock or, if possible, separated from the feedstock and drawn off from the reactor before the spent feedstock is removed. Where the oxidized co-product is valuable, it may be desirable to separate it from the spent feedstock. In other cases, it is simply part of the spent feedstock and remains for further downstream processing.

The nature of the oxidized co-product 406 may depend largely on the type of feedstock 402 that is processed. Examples of oxidized co-products 406 include, but are not limited to, biodegradable products produced from non biodegradable organic waste streams, biocompatible organics which can be biologically treated in a downstream process, oxalic acid, halogens, bromine, sulfur and sulfur containing ions, nitrogen containing ions, metal containing ions, chlorine and detoxified water. By way of example, photoelectrosynthetically processing ethanol using a PAH and sunlight forms hydrogen as the main product and acetaldehyde as the oxidized co-product 406. Processing hydrogen sulfide can yield elemental sulfur as the oxidized co-product 406. Hydrobromic acid yields bromine as the oxidized co-product 406. Decomposition of oxalic acid yields carbon dioxide as the oxidized co-product 406. Processing of tartaric acid can yield tartronaldehydic acid and carbon dioxide as co-products and/or glyoxal and carbon dioxide. Glyoxal can, in turn, be oxidized to oxalic acid and carbon dioxide.

The hydrogen from reaction vessel 404 is mixed with a carbon dioxide containing stream 408 in reaction vessel 410 in the presence of a catalyst in order to thermochemically reduce the carbon dioxide to form one or more reduction products of carbon dioxide 412 and a water co-product 414. The carbon dioxide stream 408 can come from a variety of different sources, including, but not limited to, flue gases from boilers, power plants, cement kilns, or industrial processes, natural gas containing excessive quantities of carbon dioxide, biogas containing a mixture of methane and carbon dioxide, and other gaseous streams.

The reaction between hydrogen and carbon dioxide can occur within the same reaction vessel 404 used to photoelectrosynthetically produce hydrogen. It may be performed in the headspace of vessel 404, for example, or a separate chamber of vessel 404. Alternatively, the hydrogen may be drawn off from vessel 404 and introduced into a separate reaction vessel together with the carbon dioxide containing stream 408. In the latter case, it may be possible or desirable to increase the pressure and/or temperature of the reactants in order to speed up the reaction kinetics.

The catalyst used to catalyze the reaction between hydrogen and carbon dioxide to form methane can be ruthenium, nickel or other useful catalyst known in the art for this type of reaction. Examples include, but are not limited to, noble metal or alloy supported catalysts (noble metal)/(solid acidic support), such as $Pt/SiO_2$, $Pt/\gamma-Al_2O_3$, $Pd/SiO_2$, $Pd/\gamma-Al_2O_3$, Pt/Zeolite, or $(Pt—Pd)/\gamma-Al_2O_3$, nickel on silica-alumina, ruthenium (less than 5 nm will react at room temperature). Additional examples are metal oxide catalysts, including platinum group doped cerium oxide and magnesium oxide and Ru doped cerium oxide. The type of catalyst may be selected according to desired kinetics and selectivity according to the reaction conditions during methane formation.

An exemplary catalyst used for the reaction between hydrogen and carbon dioxide to produce synthesis gas from carbon dioxide and hydrogen, in one example, can be a silica based catalysts consisting of 5% (weight) copper and 0.5% nickel. The only products are CO with 60% conversion of $CO_2$ to CO at 350° C., 150 torr, and a $CO_2/H_2$ feed ratio of ¼. Higher selectivity and conversions are achieved with greater hydrogen concentrations. The source of hydrogen for the synthesis gas can simply be additional or make up hydrogen as photoelectrosynthetically produced herein.

The synthesis gas may then be reacted on metal catalysts including iron, cobalt, ruthenium, iridium, osmium, and their combinations to produce linear alkanes with 2 or more carbons and water by way of the Fischer-Tropsch pathway.

An exemplary catalyst used for the reaction between hydrogen and carbon dioxide to produce methanol from carbon dioxide and hydrogen typically contains copper and often other metal oxides on alumina or silica supports. In one example, $Cu/ZnO/Al_2O_3$ is used in a reaction operated at between 200 and 400° C. and pressures of 10-1000 psi.

The water co-product 314 produced during thermochemical reduction of carbon dioxide for the formation of methane can be collected as pure water or, alternatively, be recycled back into vessel 404 as part of the reaction mixture. In the case where hydrogen is collected and used to produce methane in the head space of vessel 404, the water can simply condense and fall back into the reaction mixture by the force of gravity. Alternatively, if methane is produced in a separate vessel, some or all of the water co-product 314 can be returned to the reaction vessel 404 using appropriate conduits or channels known in the art.

III. Photoelectrosynthetically Active Heterostructures

Photoelectrosynthetically Active Heterostructures (PAHs) that are especially useful in the foregoing processes and systems for photoelectrosynthetically producing hydrogen from a hydrogen source and solar energy are those which are photo-electrochemically efficient and durable such that they can withstand the aqueous chemical environment of the reactor for extended periods without significant deactivation. In addition, it is desirable that they can be manufactured at a reasonable cost from relatively inexpensive elements commonly used to form semiconductors. Where more expensive metals, such as platinum group and rare earth metals are used, the relative quantity of such materials compared to the quantity of semiconductor materials can be substantially lower.

Figure 5A:
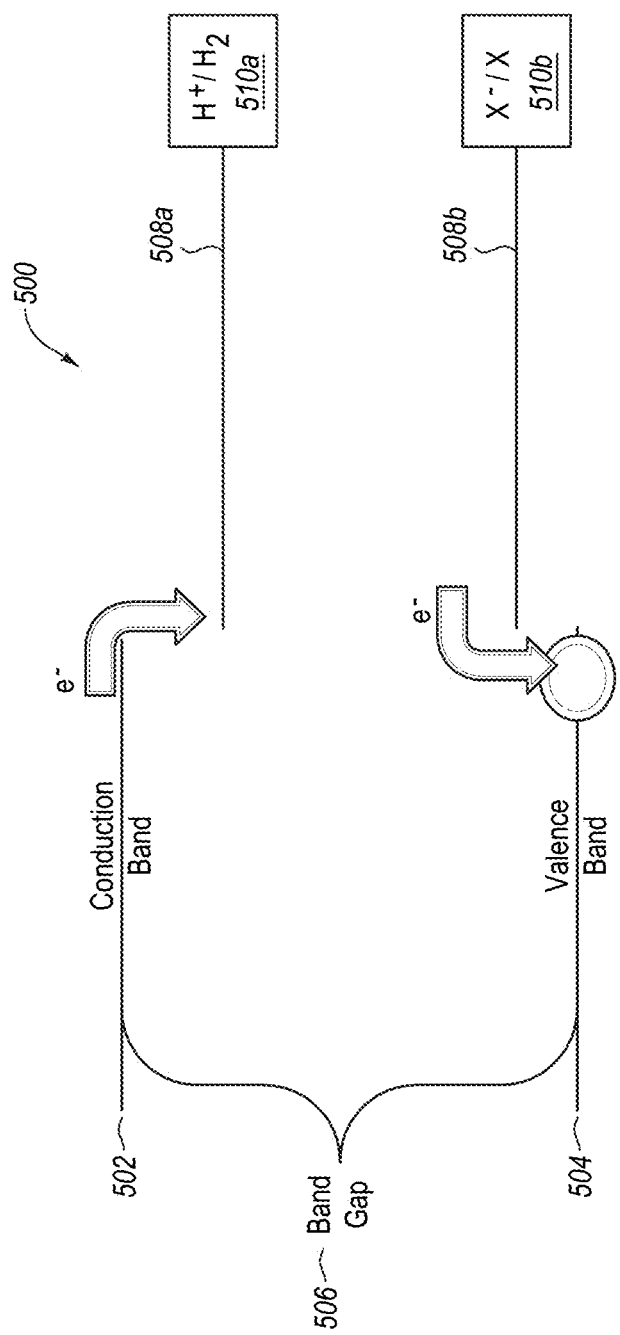
FIG. 5A is a schematic representation of an energy diagram showing how a band gap in a solar cell converts light energy into electrochemical energy to drive oxidation/reduction half reactions at the anode and cathode.
Figure 5B:
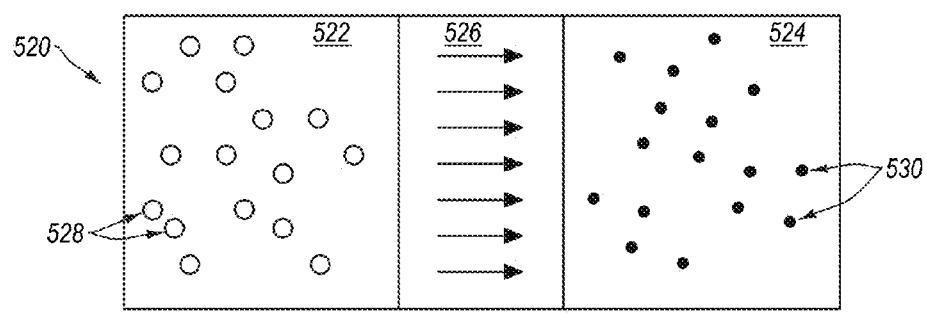
FIG. 5B is a schematic representation illustrating how placing p-type and n-type semiconductor materials adjacent to each other in a solar cell causes a buildup of electrons ($e^-$) in the n-type material and holes ($h^+$) in the p-type material.
Figure 5C:
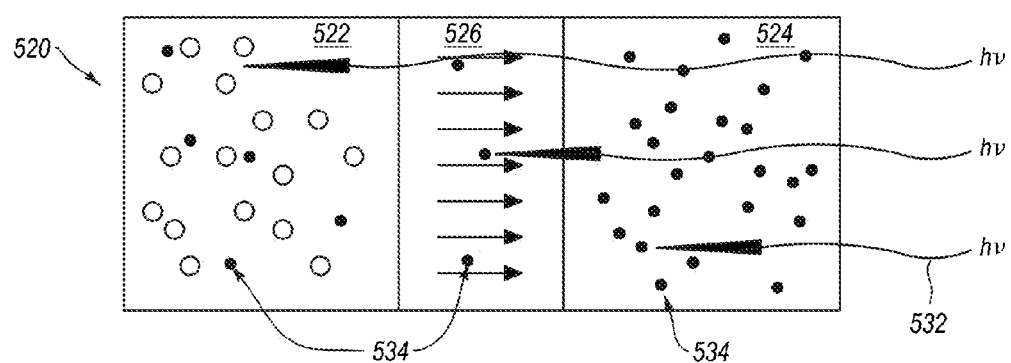
FIG. 5C is a schematic representation illustrating how incident light causes additional electrons to flow from the p-type material toward the n-type material and thereby create an electric potential capable of driving an electrochemical reaction.

By way of background, FIGS. 5A-5C schematically illustrate the underlying manner in which semiconductor materials are able to convert photonic energy into an electrical potential in order to drive an electrochemical reaction. FIG. 5A shows a simple bandgap diagram 500 of a semiconductor material having a conduction band 502 and a valence band 504. The difference between them is the band gap energy 506. A cathode 508a in electrical contact with the conduction band 502 receives electrons from the semiconductor that can be used to drive reduction half reaction 512a (e.g., hydrogen ions to hydrogen gas). An anode 508b in electrical contact with the valence band 504 receives holes from and returns electrons to the semiconductor and in so doing drives oxidation half reaction 510b (e.g., anions to oxidized co-product). The voltage between the cathode 508a and anode 508b is slightly less than the bandgap potential 506 of the semiconductor.

FIGS. 5B and 5C are references from Engineering 100, "Disorder and Coherence: From Light Bulbs to Lasers," Sep. 14, 2008, Matt Greco, Nirala Singh and Kevin Wentzke (under the supervision of Dr. John Hinckley and Prof. Jasprit Singh). FIG. 5B schematically illustrates a semiconductor 520 of a solar cell having a p-n junction comprised of a p-type semiconductor material 522 and an n-type semiconductor material 524. The n-type semiconductor has excess freely-moving negative electrons 530, and the p-type has excess positive charges, or "holes" 528 (which are really the absence of electrons, the actual carriers of positive charge, protons, do not move). When these two materials come into contact, there is an electric potential barrier 526 that forms and separates the electrons and holes, keeping them from combining. Although both sides 522, 524 have charges that move freely, the sides are electrically neutral.

FIG. 5C shows what happens when the semiconductor 520 in a solar cell is exposed to radiation energy 532. When sunlight 532 falls on the semiconductor 520, additional electrons are freed on both sides of the junction, but the potential barrier 526 only allows electrons 534 to go in one direction, from the p-type semiconductor material 522 toward the n-type semiconductor material 524, as shown by the arrows. This transfer causes a build-up of voltage across the cell, and if a circuit (including electrochemical equivalent circuits) is attached to the semiconductor 520, current will flow. The semiconductor 520 acts as a voltage source and a source of current.

Figure 6A:
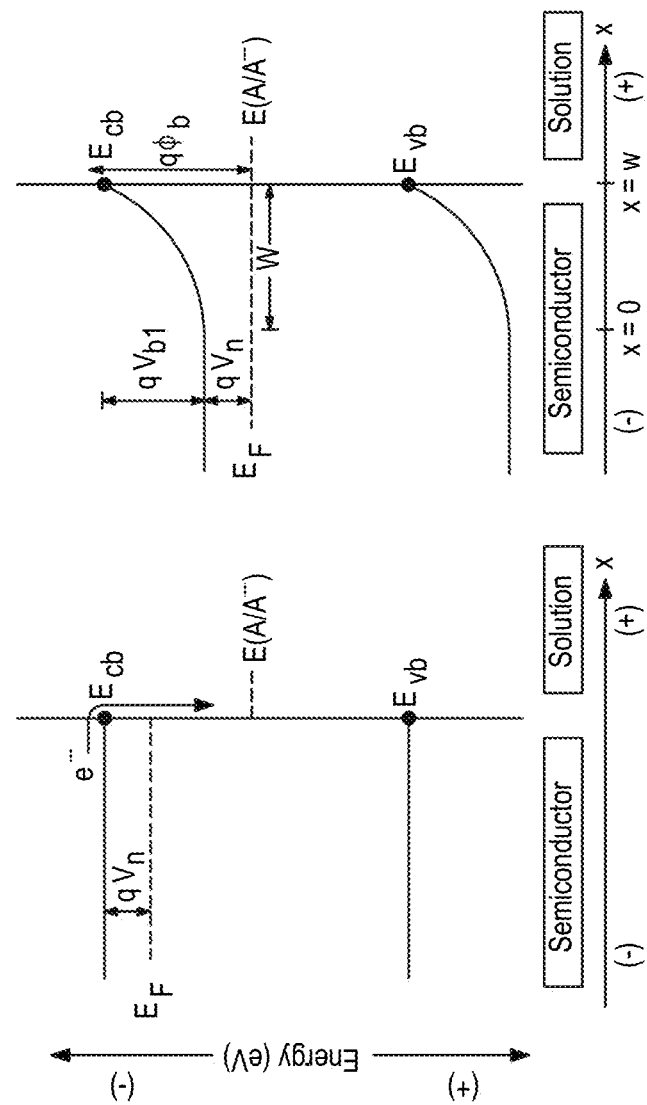
FIG. 6A is an energy diagram of semiconductor photoelectrochemistry involving an n-type semiconductor/liquid junction at equilibrium.
Figure 6B:
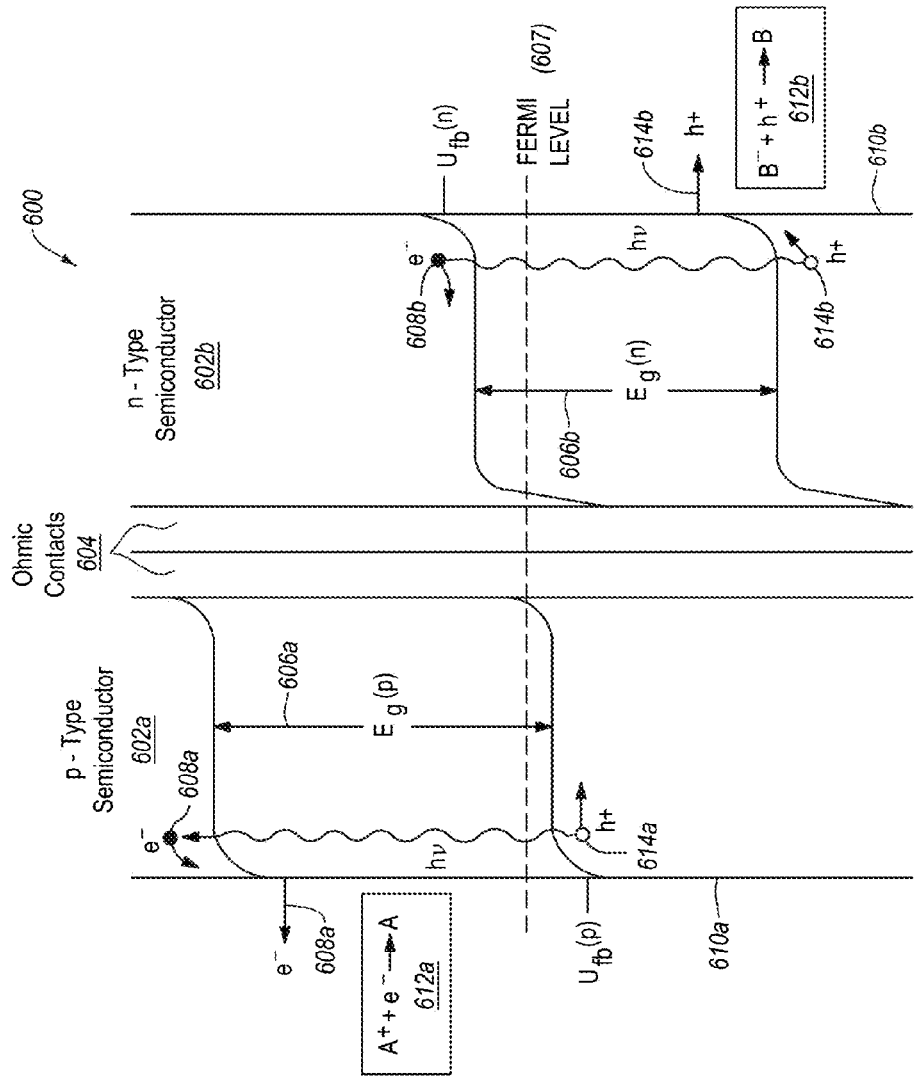
FIG. 6B is an energy level diagram for a p-n type PAH showing the flow of light-induced electrons and holes through the semiconductor materials and electrodes.
Figure 6C:
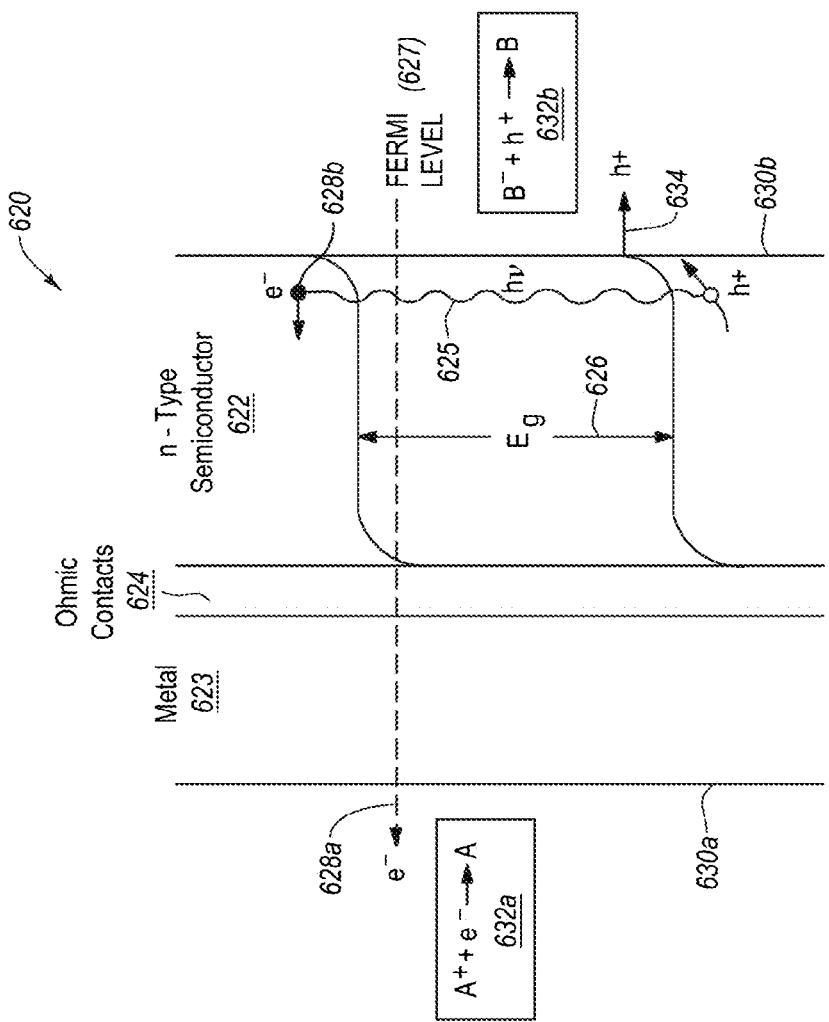
FIG. 6C is an energy level diagram for a Schottky-type PAH showing the flow of light-induced electrons and holes through the semiconductor material and electrodes.

FIG. 6A-6C are energy diagrams of semiconductors when used in connection with PAHs according to the disclosure. FIG. 6A is an energy diagram of an n-type semiconductor/liquid junction at equilibrium. In frame (a), before charge equilibrium occurs, the energy levels of the semiconductor conduction and valence bands are uniform at all points along the axis. In frame (b), after charge equilibrium has occurred, a depletion layer is formed in the semiconductor. As shown, the electric potential energy levels of $E_{cb}$ and $E_{vb}$ are dependent on the distance from the semiconductor solution interface. However, at equilibrium, the electrochemical potential is the same in the solution and at all points in the semiconductor (i.e., $E(A/A^-)=E_F$), where $E_F$ is the Fermi level. The parameter qVn is defined as the difference between $E_F$ and $E_{cb}$ in the bulk semiconductor, and $V_{bi}$ is the built-in voltage of the junction. The parameter $\varphi_b$, the barrier height, is defined as $\varphi_b=V_n=V_{bi}$.

To equilibrate Fermi levels, the semiconductor donates electrons to the electrolyte, giving itself a net positive charge near the surface of the semiconductor, and a net negative charge at the surface of the electrolyte. This causes the valence and conduction bands in the bulk of the semiconductor to lower in energy. However, the field in the region where there is a net positive charge causes the energy of the conduction band and valence band to remain higher, causing a band bending effect in what is called the depletion region.

The $E_{cb}$ and the $E_{vb}$ at the semiconductor surface remains constant relative to the Fermi level of the solution.

FIG. 6B illustrates an energy level diagram 600 for a p-n type semiconductor 602 in a reaction medium. The semiconductor 602 is comprised of a p-type semiconductor 602a and an n-type semiconductor 602b, which can be separated by one or more ohmic contacts 604. The bandgap 606 is related to the Fermi level 607. Light having energy (hv) is absorbed in both halves of the semiconductor 602, creating electron-hole pairs in the p-type semiconductor 602a and in the n-type semiconductor 602b. Electrons 608a having a potential related to the bandgap 606 are provided at cathode 610a in order to drive reduction half reaction 612a ($A^+ + e^-$). Holes 614a move away from the cathode 610a through the semiconductor materials toward the n-type semiconductor 602b. At the anode 610b, holes 614b drive oxidation half reaction 612b ($B^- + h^+$), which gives up electrons 608b, which maintain the charge balance within the semiconductor 602.

FIG. 6C illustrates an energy level diagram 620 for a Schottky-type semiconductor in a reaction medium. In this example, the semiconductor is comprised of an n-type semiconductor 622 and a metal Schottky barrier 623, which can be separated by one or more ohmic contacts 624. The bandgap 626 is related to the Fermi level 627. Light 625 having energy (hv) greater than the bandgap 626 is absorbed by semiconductor 622, creating electron-hole pairs in the n-type semiconductor 622. Electrons 628a having a potential related to the bandgap 626 are provided at cathode 630a in order to drive the reduction half reaction 632a ($A^+ + e^-$). Holes 634 move from the n-type semiconductor 622 toward the anode 630b to drive the oxidation half reaction 632b ($B^- + h^+$), which gives up electrons 628b, and which maintain the charge balance within semiconductor 622. In the case where the semiconductor is comprised of a p-type semiconductor, the flow of electrons and holes is reversed.

Figure 7A:
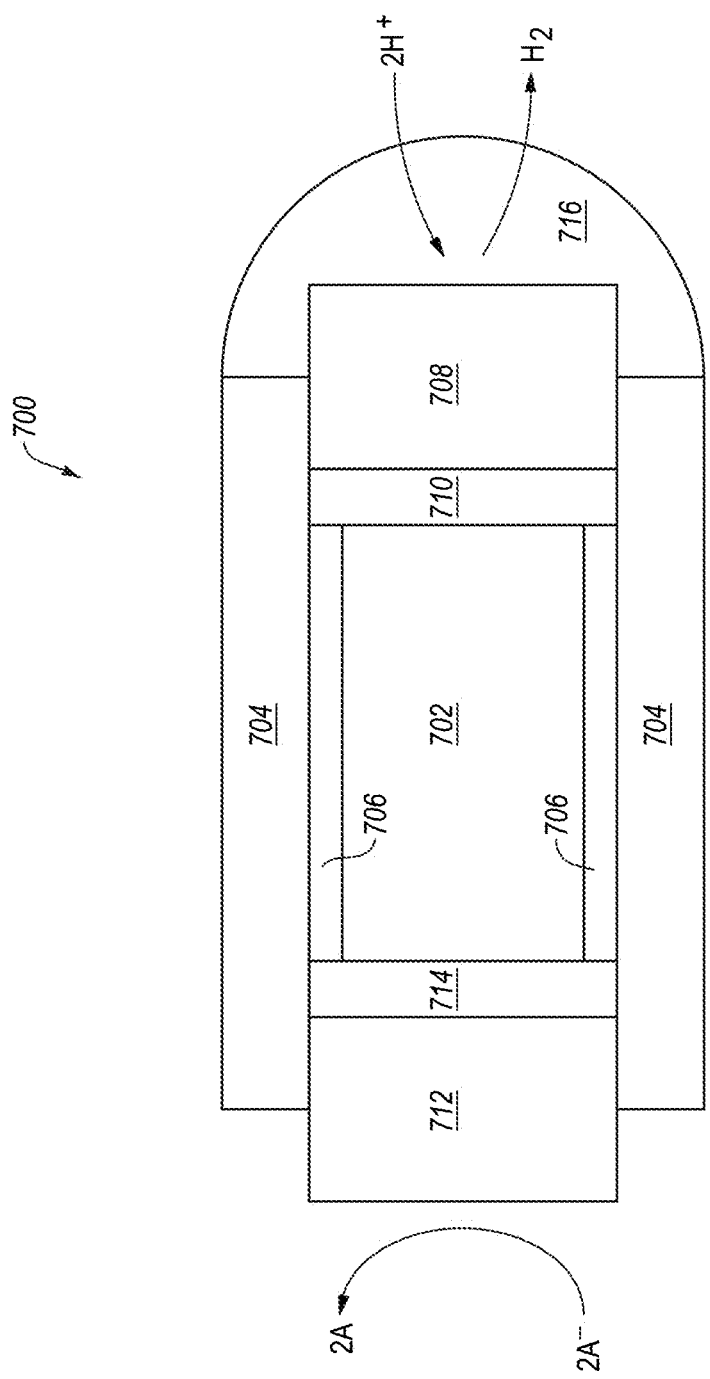
FIG. 7A is a cross-sectional schematic illustration of a PAH according to the disclosure for use in converting light energy into electrochemical energy in order to drive oxidation/reduction reactions in a reaction mixture.
Figure 7B:
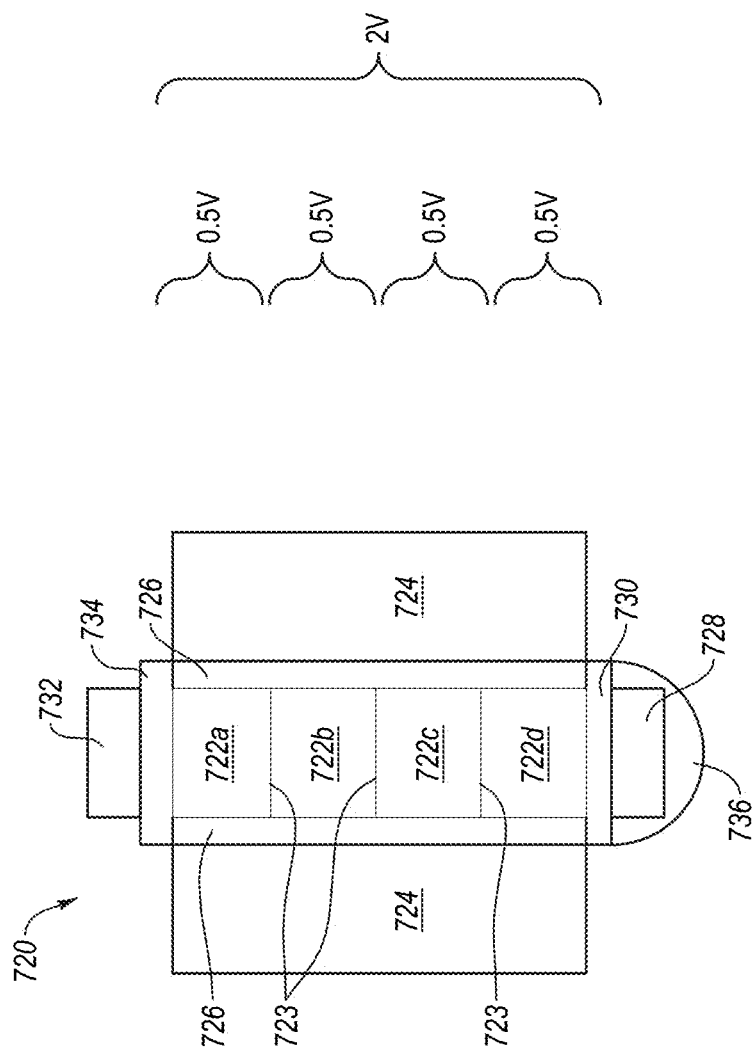
FIG. 7B is a cross-sectional schematic illustration of a multi-cell PAH according to the disclosure for use in converting light energy into electrochemical energy of higher voltage in order to drive oxidation/reduction reactions in a reaction mixture.

FIGS. 7A and 7B illustrate exemplary PAHs according to the disclosure. FIG. 7A is a schematic cross-sectional representation of a PAH 700 that includes a semiconductor absorber 702 for absorbing light energy. The semiconductor absorber 702 may comprise one or more types of semiconductor materials (e.g., p-type and/or n-type) to form one or more p-n junctions or one or more Schottky junctions.

Examples of suitable p-type semiconductor materials include, but are not limited to intrinsic or p-doped SnS, ZnS, CdS, CdSe, CdTe, $Cu_2S$, $WS_2$, $Cu_xO$, $Cu_2ZnSnS_4$, $CuIn_xGa_{1-x}Se_2$, GaN, InP, SiC, and others selected from the classes of doped (p-type) or undoped i) elemental semiconductors including Si, and Ge, and ii) compound semiconductors including, metal sulfides, selenides, arsenides, nitrides, antinomides, phosphides, oxides, tellurides, and their mixtures containing respectively, sulfur (S) selenium (Se), arsenic (As), antimony (Sb), nitrogen (N), oxygen (O) tellurium (Te), and/or phosphorus (P) as one or more electronegative element(s) A, and one or more metals, M, of the form $M_nA_x$ where M is one or a combination of elements including but not limited to Cu, Ga, Ge, Si, Zn, Sn, W, In, Ni, Fe, Mo, Bi, Sb, Mg.

Examples of suitable n-type semiconductor materials include, but are not limited to intrinsic or n-doped InS, CdTe, CdS, CdSe, CdTe, $Cu_2S$, $WS_2$, $Cu_xO$, $Cu_2ZnSnS_4$, $CuIn_xGa_{1-x}Se_2$, GaN, InP, SiC, and others selected from the classes of doped (n-type) or undoped i) elemental semiconductors including Si, and Ge, and ii) compound semiconductors including, metal sulfides, selenides, arsenides, nitrides, antinomides, phosphides, oxides, tellurides, and their mixtures containing respectively, sulfur (S), selenium (Se), arsenic (As), antimony (Sb), nitrogen (N), oxygen (O), tellurium (Te), and/or phosphorus (P) as one or more electronegative element(s) (A), and one or more metals (M), of the form $M_nA_x$ where M is one or a combination of elements including but not limited to Cu, Ga, Ge, Si, Zn, Sn, W, In, Ni, Fe, Mo, Bi, Sb, Mg.

A protective coating 704 covers semiconductor absorber 702 and contacts the semiconductor at interface 706 and protects absorber 702 from corrosion or degradation. The protective coating is advantageously transparent to light energy that is to be absorbed by semiconductor absorber 702 and may comprises any suitable electrically insulating material, including, but not limited to $Al_2O_3$, $SiO_2$, ZrO, $AlF_3$, and $TiF_2$, ZnO, and $TiO_2$.

The interface 706 where the semiconductor contacts the protective coating is specifically designed to minimize electron/hole recombination and may be formed by either pretreatment of the semiconductor or protective coating material to eliminate charge recombination sites. A specific example is the application of a thin layer of ZnO by atomic layer deposition from a chemical vapor precursor to serve as the interface between an alumina protective coating and the semiconductor surface to minimize surface electronic trap states.

A cathode 708 is positioned adjacent to semiconductor absorber 702 at interface 710. The cathode serves as an electrocatalyst to efficiently transfer electrons from the cathode bulk to electron acceptor reactants in solutions. Suitable materials for use in forming cathode 708 include, but are not limited to, conductors comprised of platinum group metals such as Pt and Au, transition metals, transition metal oxides (e.g. NiO), metal carbides (e.g., WC), metal sulfides (e.g. $MoS_2$), and electrical conducting carbon containing materials, such as graphite, graphene, and carbon nanotubes.

A selectively permeable barrier 716 covers the cathode 708, which allows only molecular hydrogen to pass and, in systems used with acidic media, hydrogen ions (or hydronium ions) and molecular hydrogen and, in systems used in basic media, water and hydroxyl ions. The barrier prevents the reduction of other species (e.g. products from the anode) in the reaction mixture on the cathode which would decrease the efficiency of the PAH. The selectively permeable barrier layer 716 is an electrical insulator and may be comprised of hydrogen permeable barrier materials which are also permeable to the other species used for other applications and known by those skilled in the art, examples of which include chromium (III) oxide ($Cr_2O_3$), Nafion membranes (made from sulfonated tetrafluoroethylene-based fluoropolymer-copolymers), and hydrogen permeable polymers such as acrylics, also an element of the invention are new metal oxide hydrogen ion/molecule conductors comprised of mixtures of metal oxides, including $WCrO_x$, and $WZrCeO_x$.

The interface 710 between the cathode 708 and the semiconductor 702 provides an electrically conductive pathway between the semiconductor and the electroreduction catalysts cathode. To maintain a high efficiency this interface must minimize the resistance and charge recombination. The specific material will depend upon the type of semiconductor and the cathode material. For example, if the semiconductor were n-type silicon and the cathode were platinum the interface could be hydrogen terminated silicon, Si—H, prepared by treating the Si in dilute buffered HF solution with a layer of Ti to serve as an ohmic contact or (n-Si/H/Ti/Pt).

An anode 712 is positioned on the opposite side of semiconductor absorber 702 at interface 714. The anode serves as an electro-oxidation catalyst to facilitate the chemistry and electron transfer from the electron donating reactants which are oxidized to the cathode bulk. The materials which may be used to form the anode 712 include, but are not limited to conductors comprised of metals, their oxides, and their mixtures from metals including Ru, Ag, V, W, Fe, Ni, Pt, Pd, Ir, Cr, Mn, Cu, Ti, and metal sulfides (e.g., $MoS_2$) and electrical conducting carbon containing materials such as graphite, graphene, and carbon nanotubes.

The interface 714 between the anode 712 and the semiconductor 702 provides an electrically conductive pathway between the semiconductor and the electro-oxidation catalyst anode. To maintain a high efficiency this interface must minimize the resistance and charge recombination. The specific material will depend upon the type of semiconductor and the anode material. For example, if the semiconductor were n-type silicon and the anode were a platinum Schottky barrier, the interface can be hydrogen terminated silicon (Si—H), prepared by treating the Si in dilute buffered HF solution for a junction of the form n-Si/H/Pt. Alternatively, 1-2 atomic layers of aluminum or Mg may be applied at the interface of p-type copper oxide and a ruthenium oxide anode.

As further illustrated, the reduction half reaction of hydrogen ions to form hydrogen gas occurs at the cathode 708, and the oxidation half reaction to form the oxidized co-product occurs at the anode 712. While the oxidation half reaction is illustrated as anion ($A^-$) being oxidized to product (A), it could be understood that any molecule of any valence can be reduced to any oxidized product of reduced valence and/or lower hydrogen content.

FIG. 7B shows an alternative embodiment of a PAH 720 having multiple light absorbers 722a, 722b, 722c, 722d are connected in series by semiconductor contacts 723. Each light absorber 722 produces it own voltage potential (e.g., 0.5V as shown), and when connected in series, the total voltage will be the sum of individual voltages (e.g., 2.0V as shown). The light absorbers 722 can be p-n junctions and/or Schottky junctions.

A protective covering 724 is attached to light absorbers 722 at interface 726 and protects light absorbers 722 from corrosion or other deleterious reactions during use. A cathode 728 is attached at one end of the light absorber series 722 by interface 730 an anode 732 is attached to the opposite end of the light absorber series 722 by interface 734. A hydrogen-permeable coating 736 covers cathode 730.

FIGS. 8A-8D illustrate exemplary oxidation/reduction reactions that can occur at the cathode and anode of a PAH according to the disclosure. In the reaction shown in FIG. 8A, ethanol ($C_2H_6O$) is photoelectrosynthetically oxidized to acetaldehyde ($C_2H_4O$) at the anode as co-product, and hydrogen gas ($H_2$) is produced at the cathode as the main product. Because the reaction environment is alkaline in this example, water ($H_2O$) is reduced to hydrogen gas ($H_2$) and hydroxyl ions ($OH^-$), and hydrogen ions ($H^+$) are removed from ethanol when oxidized to acetaldehyde and combine with hydroxyl ions ($OH^-$) to maintain charge balance in the reaction mixture.

Figure 8A:
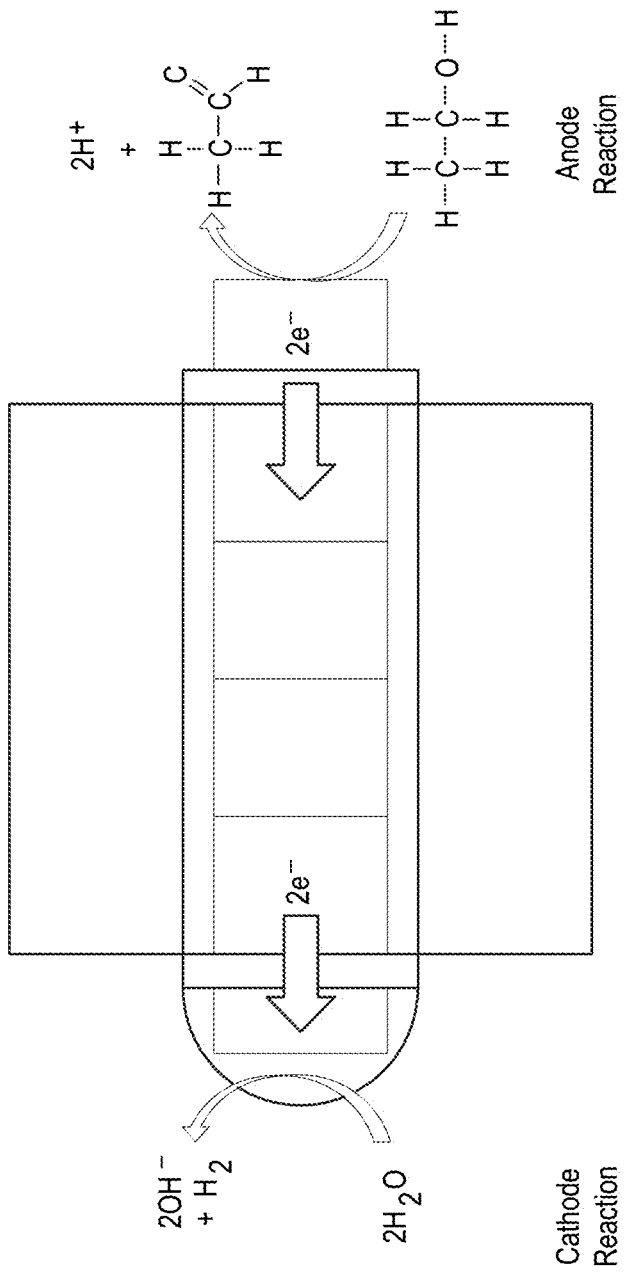
FIGS. 8A-8D schematically illustrate various exemplary oxidation/reduction half reactions at the anode and cathode of a PAH according to the disclosure.
Figure 8B:
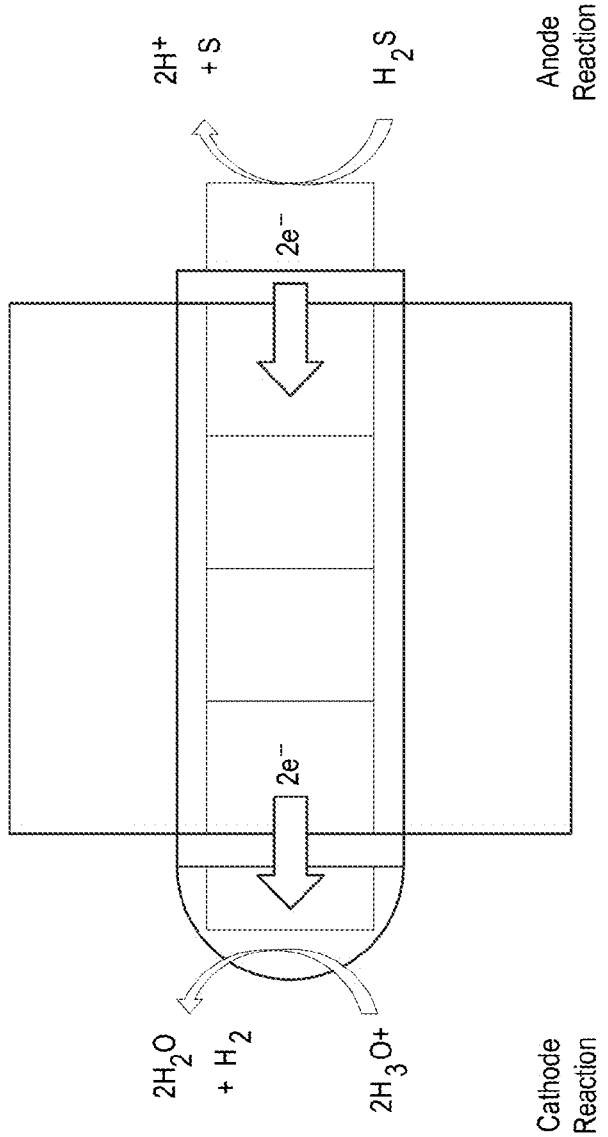

In the reaction shown in FIG. 8B, hydrogen sulfide ($H_2S$) is photoelectrosynthetically oxidized to elemental sulfur at the anode as co-product, and hydrogen gas is produced at the cathode as the main product. Because the reaction mixture is acidic in this example, hydronium ions ($H_3O^+$) are reduced to hydrogen gas ($H_2$) and water ($H_2O$), and hydrogen ions ($H^+$) are removed from hydrogen sulfide when oxidized to elemental sulfur and combine with water to maintain charge balance and acidity in the reaction mixture.

Figure 8C:
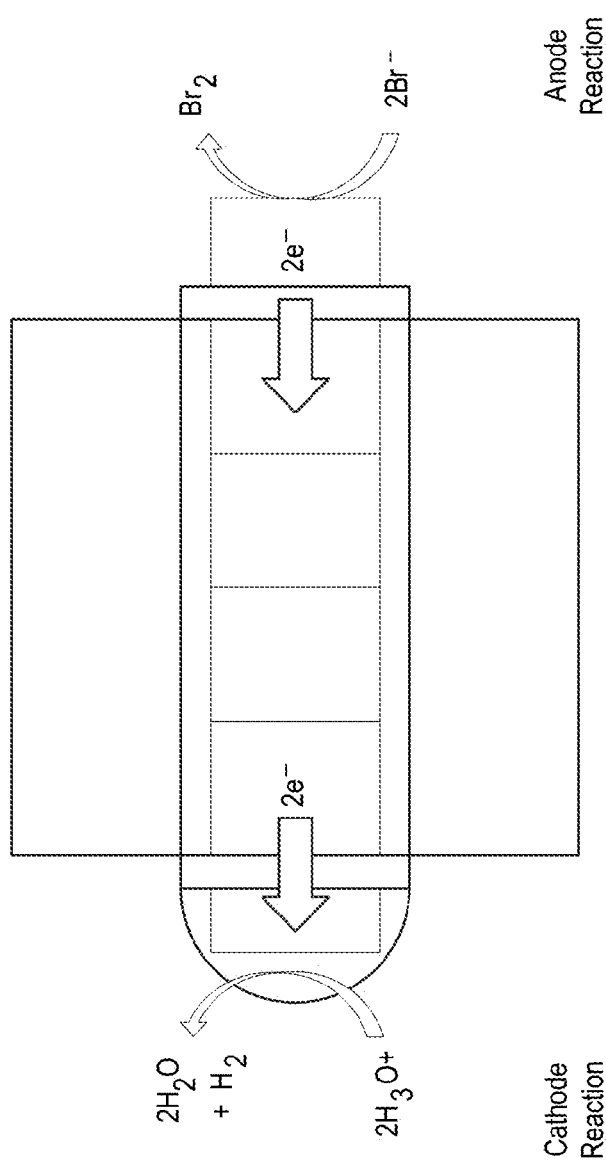

In the reaction shown in FIG. 8C, hydrobromic acid (HBr) is photoelectrosynthetically oxidized to elemental bromine ($Br_2$) at the anode as co-product, and hydrogen gas is produced at the cathode as the main product. Because the reaction mixture is acidic in this example, hydronium ions ($H_3O^+$) are reduced to hydrogen gas ($H_2$) and water ($H_2O$), and hydrogen ions ($H^+$) are removed from hydrobromic acid when oxidized to elemental bromine and combine with water to maintain charge balance and acidity in the reaction mixture.

Figure 8D:
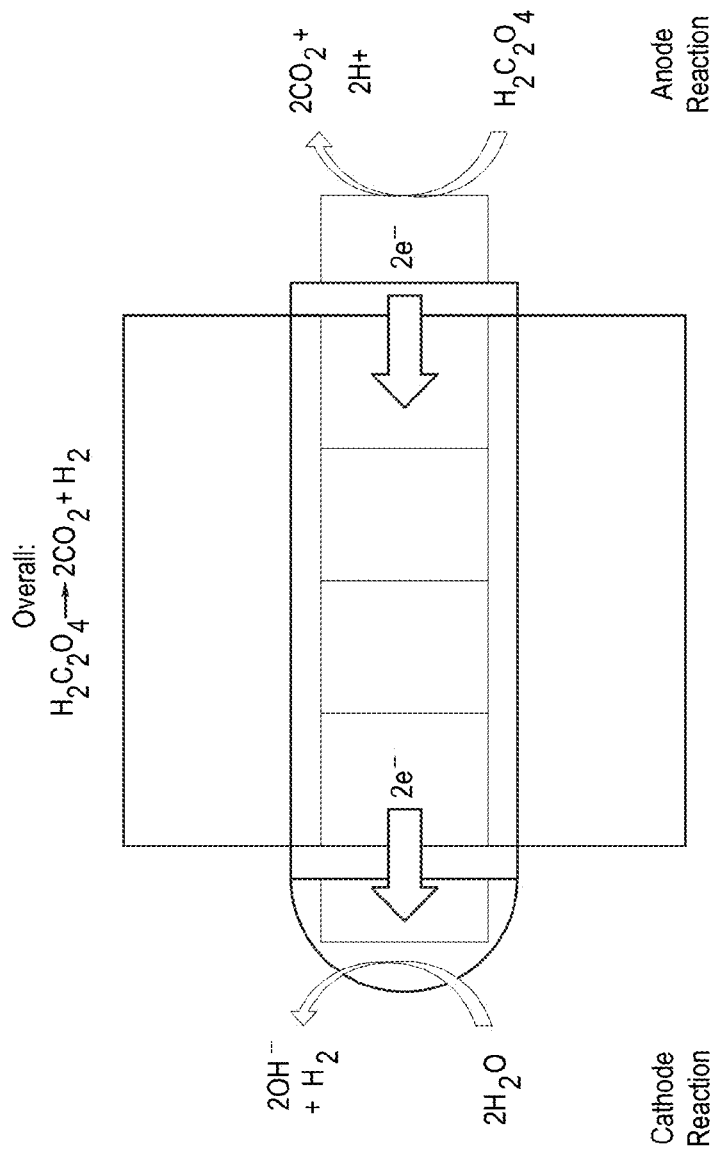

In the reaction shown in FIG. 8D, oxalic acid ($H_2C_2O_4$) is photoelectrosynthetically oxidized to carbon dioxide ($CO_2$) at the anode as co-product, and hydrogen gas is produced at the cathode as the main product. Because the reaction mixture is basic in this example, water ($H_2O$) is reduced to hydrogen gas ($H_2$) and hydroxyl ions ($OH^-$), and hydrogen ions ($H^+$) are removed from oxalic acid when oxidized to carbon dioxide and combine with hydroxyl ions to maintain charge balance in the reaction mixture.

Figure 9A:
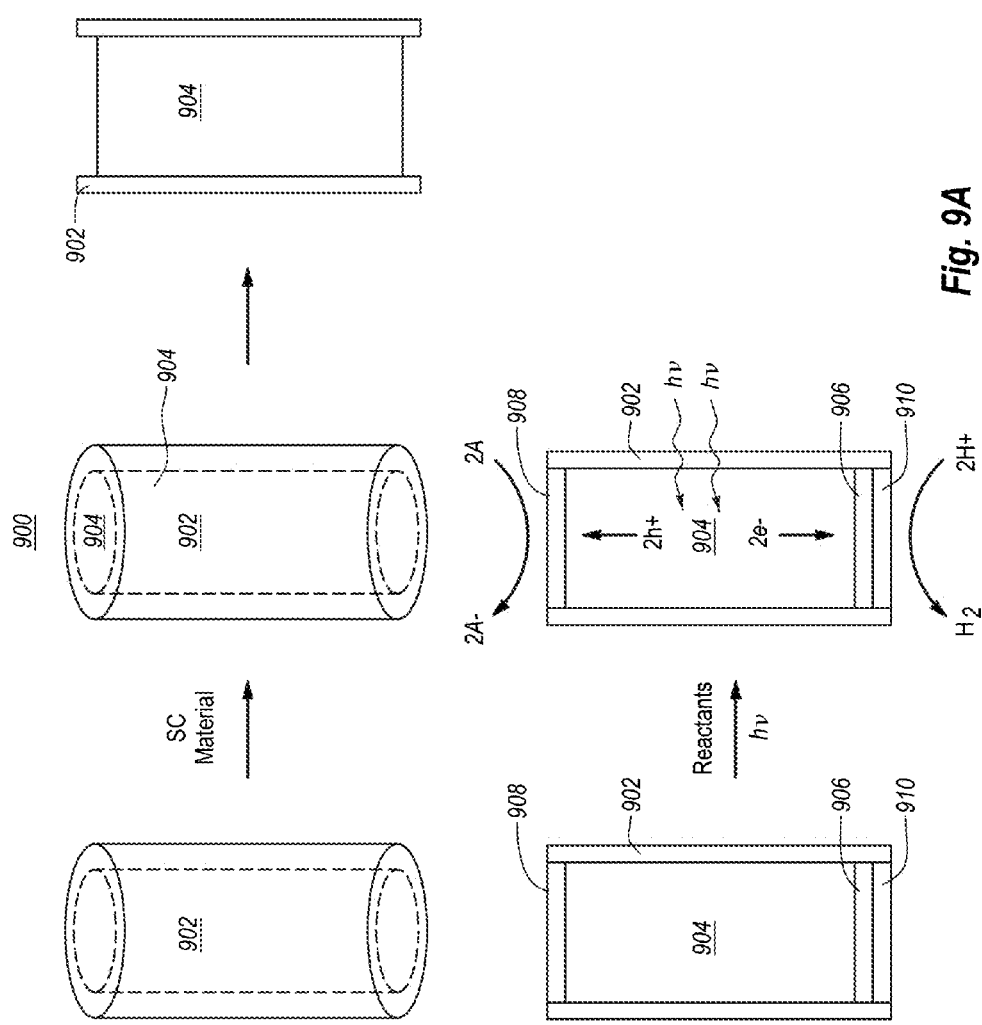
FIG. 9A schematically illustrates a process for manufacturing a cylindrical PAH according to the invention that can drive half reactions at the anode and cathode when exposed to light.
Figure 9B:
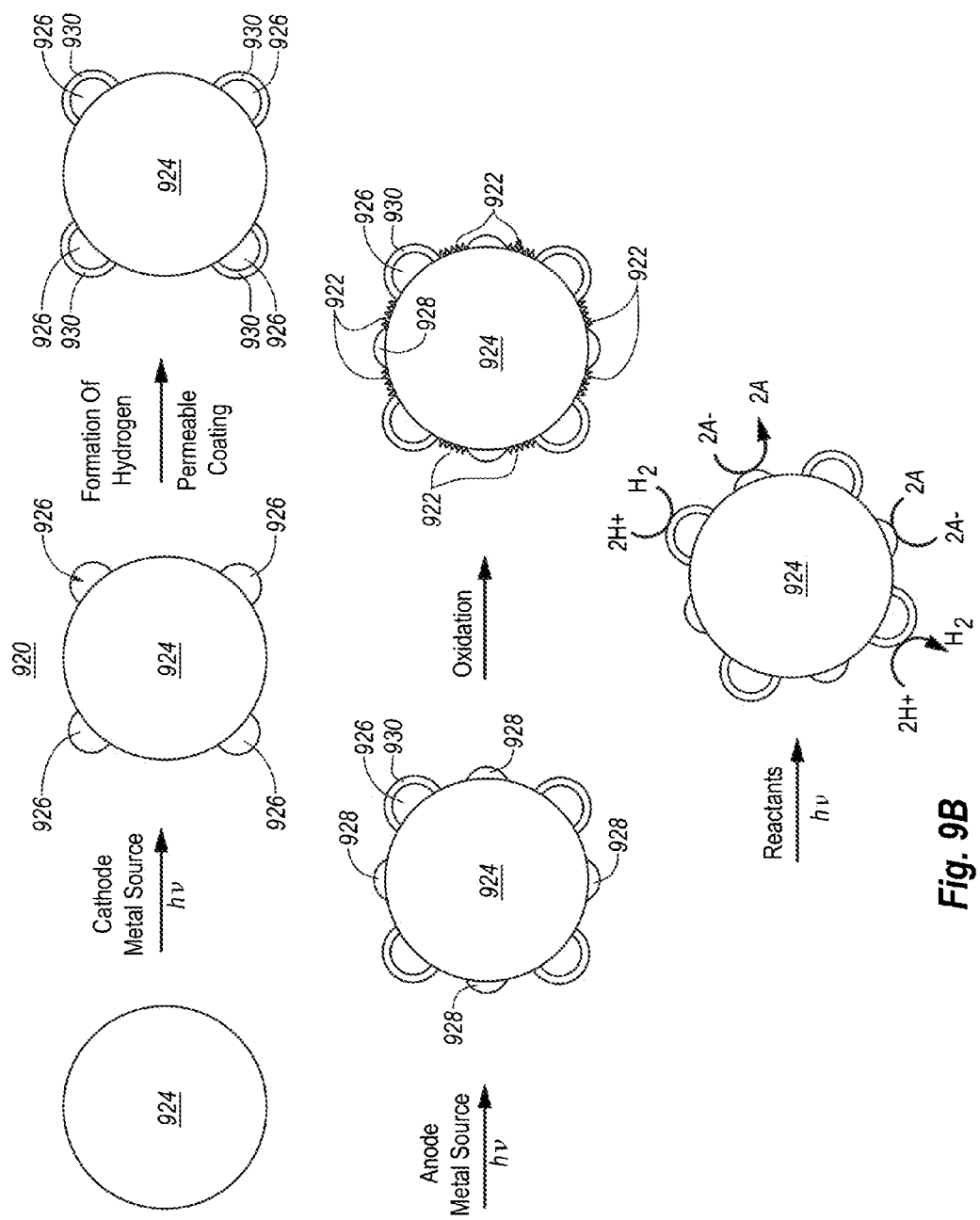
FIG. 9B schematically illustrates a process for manufacturing a nano-sized particulate PAH according to the invention that can drive half reactions at the anodes and cathodes when exposed to light.
Figure 9C:
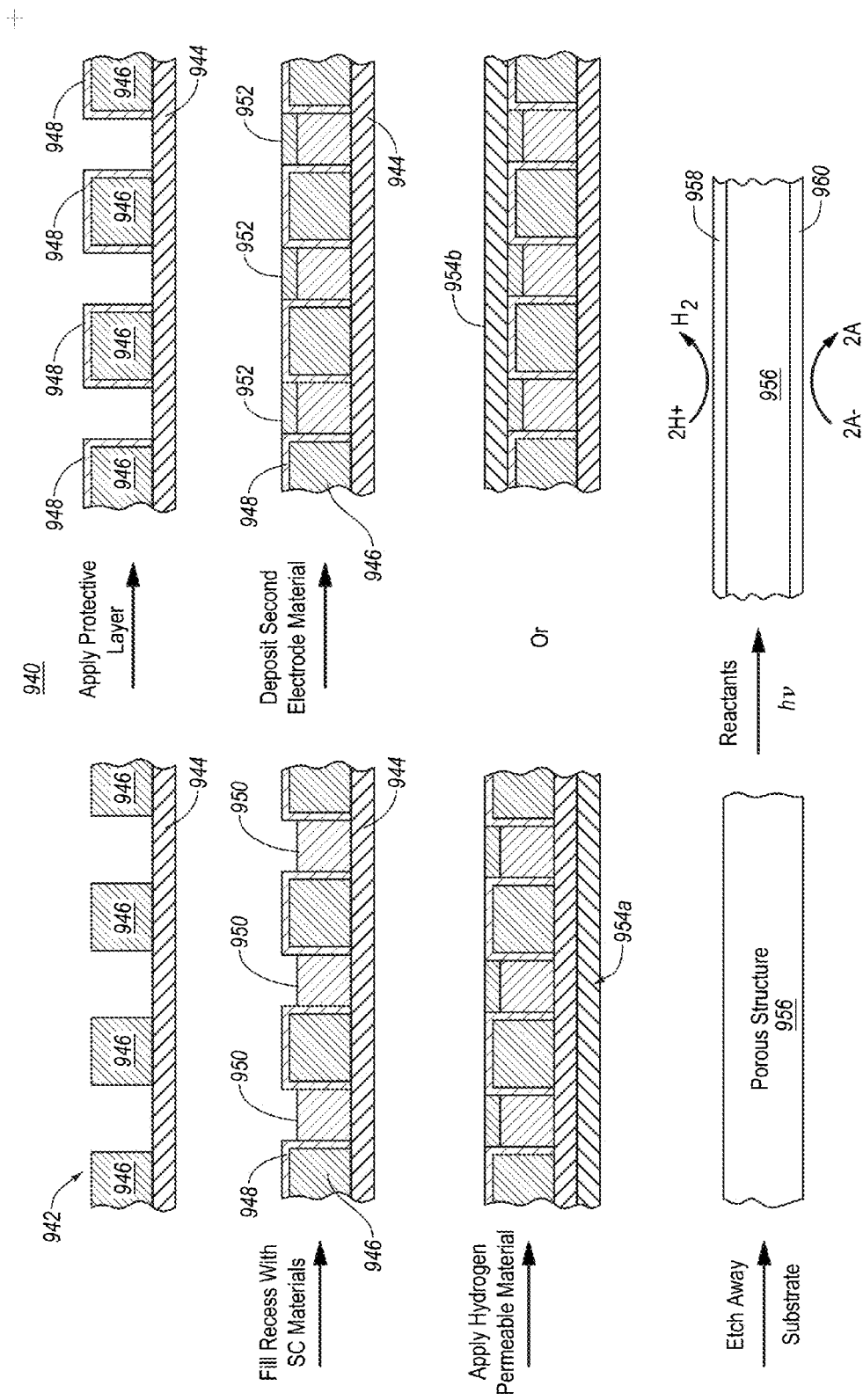
FIG. 9C schematically illustrates a process for manufacturing a sheet-like PAH according to the invention that can drive half reactions at the anodes and cathodes when exposed to light.

FIGS. 9A-9C illustrate how exemplary PAHs according to the disclosure can be manufactured and used to drive desired oxidation/reduction reactions. FIG. 9A illustrates in a schematic process diagram 900 in the formation of PAHs which may be substantially cylindrical similar to those shown in FIGS. 7A-8D described above. Initially, a structure 902 formed of inert insulating material (e.g., alumina) is provided, which includes a hollow interior cavity. The cavity is filled with one or more types of semiconductor materials 904 (e.g., p-type and/or n-type) in order to form one or more p-n junctions and/or one or more Schottky junctions within the hollow cavity of tubular structure 902. This may be performed by any method known in the art for forming semiconductor junctions, including, but not limited to electrodeposition, chemical deposition and physical vapor deposition. In one specific example, the cylinder is silica and is provided atop an electrically conducting surface consisting of copper. The semiconductor material 904 comprised of CdS is electrodeposited into the cylinder. Then the copper etched away leaving free floating CdS filled cylinders.

A cathode layer 906 is formed on an exposed side of semiconductor material(s) 904 (e.g., by one or more of photodeposition, electrodeposition, annealing or heat treating steps), and an anode layer 908 is formed on the other exposed side of semiconductor material(s) 904 (e.g., by electrodeposition or photodeposition followed by oxidation). A hydrogen permeable membrane 910 is applied over the cathode layer 906 in order to prevent back reaction and/or formation of undesirable reduction products.

A specific example would be to place the CdS filled cylinders in an electrolyte solution with $H_2PtCl_6$ and a sacrificial oxidant (methanol) and exposing the solution to light. Platinum metal would be photoreduced on the semiconductor surface to form the cathode 906. The electrolyte would then be changed to chromium sulfate/chloride and methanol and the solution exposed to light. Chromium would be photoelectroreduced onto the Pt, forming a thin layer of metal. Then the solution would be changed to nickel acetate and a sacrificial electron acceptor and the solution exposed to light. NiOOH is anodically deposited from light generated holes to produce the precursor to layer 908. The PAH is then heat treated to convert the chromium on the Pt layer to chromium oxide to form layer 910 and the NiOOH to NiO to form layer 908.

FIG. 9B illustrates an exemplary flow diagram 920 for use in forming nano-sized particulate PAHs. First, a semiconductor particle 924 is formed or provided and reacted with a cathode metal source to form cathode particles 926 on the surface of the semiconductor particle 924. In one example, chloroplatinic acid ($H_2PtCl_6$) is photochemically reduced in a reaction medium that includes methanol as the sacrificial oxidized species to form the cathode metal clusters 926 on p-type silicon particles which were initially hydrogen terminated by treatment with HF. The spacing of the cathode metal clusters 926 is controlled by forming the initial or seed particles, by limiting the amount of light used and use of low concentrations of chloroplatinic acid to initially form the platinum seed particles. Thereafter, the reduced platinum metal atoms will preferentially deposit over the seed particles and grow the cathode metal clusters 926.

A hydrogen permeable coating 930 is then selectively applied over the cathode metal clusters 926. This may be performed, for example, in a multi-step process that includes a first step of photochemically reducing copper metal onto the surface of the cathode metal clusters 926, followed by electroless exchange of copper metal atoms with chromium metal ions to form chromium metal, followed by oxidation of the chromium metal to form chromium oxide. Alternatively, the hydrogen permeable coating 930 can be formed over the cathode metal clusters 926 in a subsequent step after formation of the anode metal clusters 928. A specific example is to deposit onto the reduced Pt cathode metal catalysts chromium metal by photoelectrodeposition from a chromium sulfate/chloride solution.

To form the anode metal clusters 928, an anode metal source is provided and reduced onto the surface of the semiconductor particle 924. In one example, ruthenium chloride ($RuCl_3$) is partially hydrolyzed in an acid medium in the presence of light to form ruthenium hydroxide, which is later dehydrated to form the ruthenium oxide anode. In another example, ruthenium acetate is used as the source of anodic deposition of ruthenium oxyhydroxide by exposure of the particles in ruthenium acetate solution to light.

The semiconductor particle 924 with attached cathode particles 926 and anode particles 928 is oxidized (e.g., using an oxidizer and heat in an aqueous medium). For example, if the semiconductor particle 924 includes silicon, oxidation forms a passivated layer of silicon dioxide on all previously unprotected semiconductor surface not covered by cathode particles 926 and anode particles 928 in order to form a protective layer 922 that protects the semiconductor material 924 during use. In the example above, the oxidation step finishes forming the chromium oxide on the cathode and the ruthenium oxide on the anode.

In use, when the PAH is exposed to light energy that equals or exceeds the bandgap energy of the PAH, the cathode particles 926 drive the reduction half reaction in which hydrogen ions are reduced to hydrogen gas. The anode particles 928 drive the oxidation half reaction using molecules in the waste stream material to form an oxidized co-product.

FIG. 9C illustrates an exemplary process diagram 940 for use in forming sheet-like PAHs. First, a layered conducting layer 944 is provided, on which an insulating honeycomb structure 946 is deposited to form cavities into which materials can be deposited and processed, alternatively the honeycomb structure 946 can be formed from a single conducting substrate such as aluminum which can be anodized to form insulating partitions 946 and open pores using methods know to the art and the assembly laminated or formed on a conductor. As shown in FIG. 9C, the altered layered sheet comprises a non-oxidized conducting layer 944 (e.g., gold) and an insulating layer 946 having spaced-apart cavities.

In a first step, a protective layer 948 ($AlF_3$) may be formed onto the surface of insulating structures 946. In a second step, the remaining recesses are filled with one or more types of conductors (anodes/cathode, interfaces, semiconductor material (e.g., one or more of p-type or n-type)) to form one or more absorber substructure cells or regions 950. Thereafter, a second electrode material 952 is deposited onto the exposed surface of the semiconductor material. Whether the second electrode material 952 functions as a cathode or anode depends on the type of semiconductor material (p-type or n-type) that is adjacent to the second electrode material 952. The interfaces between the anode-semiconductor and cathode semiconductor and semiconductor protective coating will depend on the types of semiconductor.

In a third step, a hydrogen permeable material 954 is applied to the surface of the sheet where the cathode is located. In the case where the non-oxidized metal layer 944 serves as the cathode, a hydrogen permeable layer 954a is applied over the exposed surface of the non-oxidized metal layer 944. Alternatively, in the case where the second electrode material 952 serves as the cathode, a hydrogen permeable layer 954b is applied over the exposed surface of the second electrode material 952.

Thereafter, at least a portion of the oxidized metal layer 946 can be etched to form a porous structure 956 having greater surface area and transparency for absorbing incident light. In use, when the PAH is exposed to light energy that equals or exceeds the bandgap energy of the PAH, the cathode layer or regions 958 drive the reduction half reaction in which hydrogen ions are reduced to hydrogen gas. The anode layer or regions 960 drive the oxidation half reaction using molecules in the waste stream material to form an oxidized co-product.

Figure 10A:
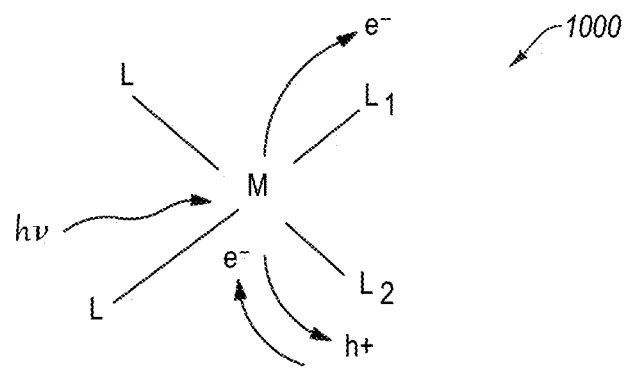
FIG. 10A illustrates a generic molecular absorber for converting light energy into electrochemical energy when exposed to light.
Figure 10B:
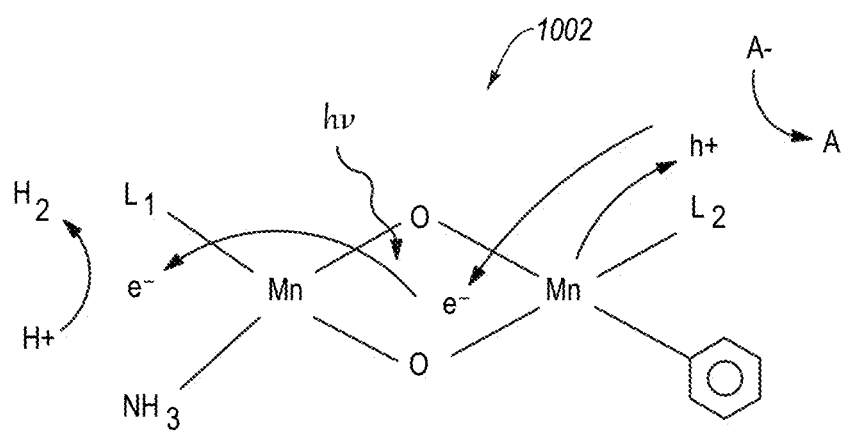
FIG. 10B illustrates another molecular absorber for converting light energy into electrochemical energy when exposed to light.

FIGS. 10A and 10B illustrate alternative examples of molecular light absorbers. Molecular light absorbers are designed have the same function as chlorophyll in plants in order to drive desired oxidation/reduction reactions when exposed to light energy. They play the same role as the semiconductor in the previously described PAH. One form of PAH described herein uses the molecular light absorber to convert sunlight into electrons and holes and either transfer the electrons and holes through interfaces connected to anodes and cathodes similar to those described above or to molecular level catalytic centers within the absorber.

FIG. 10A depicts a generic molecular light absorber 1000 having a metal center (M) attached to ligands (e.g., 4), which are able to create delocalization of electrons and buildup of charge potential when exposed to light energy. As shown, incident light of energy, hv, causes an electron to be discharged in the vicinity of ligand $L_1$ and a hole to be discharged in the vicinity of ligand L2.

FIG. 10B depicts a molecular light absorber species 1002 based on manganese oxalate coordinated or complexed with ligands $L_1$, $L_2$, phenyl, and ammonia, which are able to create delocalization of electrons and buildup of charge potential when exposed to light energy. The ammonia and phenyl may be replaced by inorganics providing similar electronic modifications. As shown, incident light energy of energy, hv, causes an electron to be discharged in the vicinity of ligand $L_1$ in order to drive the reduction of hydrogen ions to hydrogen. A hole is discharged in the vicinity of ligand $L_2$ in order to drive the oxidation of anion $A^-$ (or other reactant) to A or other reduced oxidation co-product species.

Figure 11A:
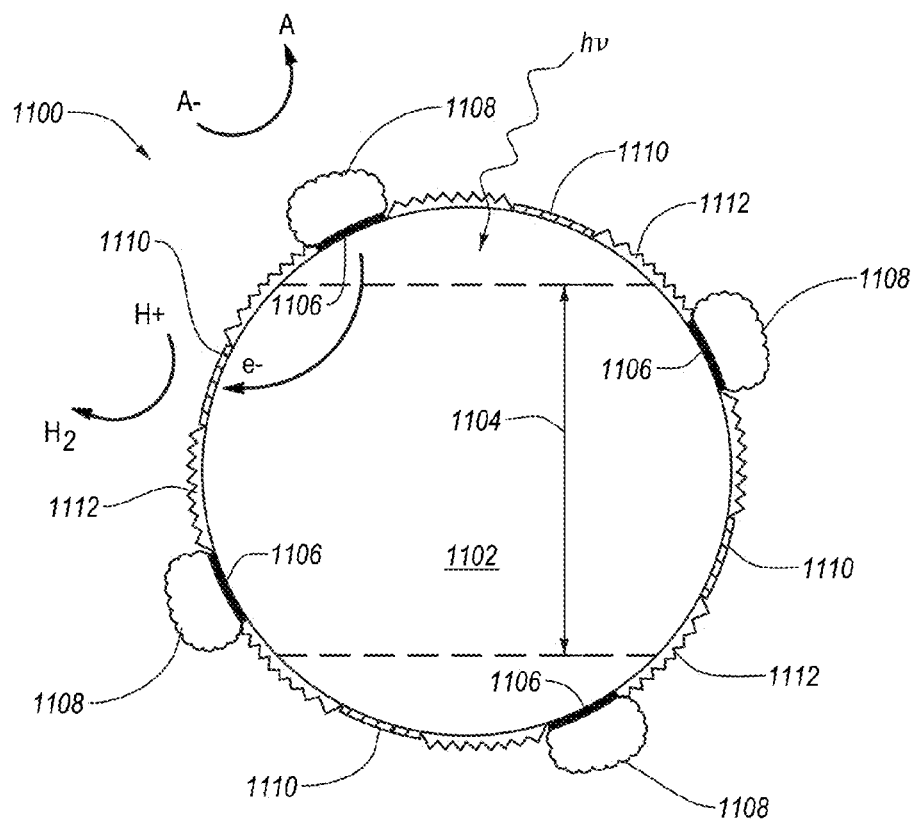
FIG. 11A schematically illustrates an exemplary PAH that includes molecular absorber clusters attached to a semiconductor material for converting light energy into electrochemical energy through ballistic charge transfer.
Figure 11B:
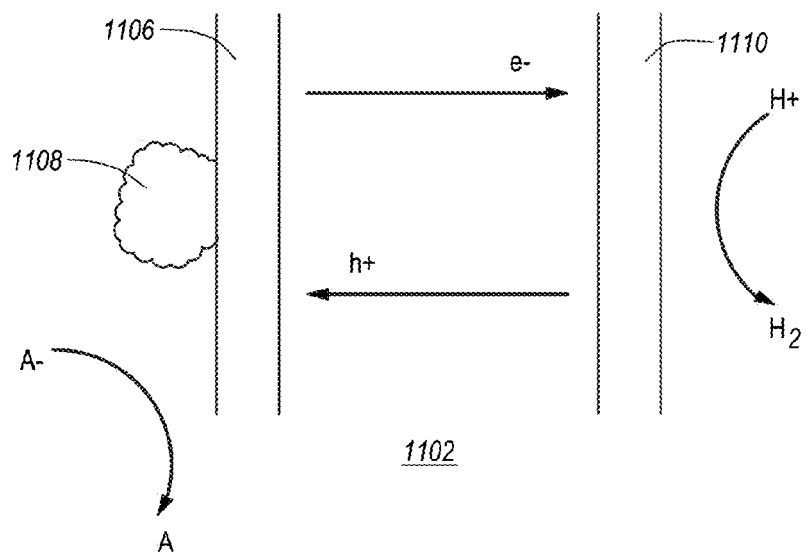
FIG. 11B is a diagram that schematically illustrates the ballistic charge transfer between the molecular absorber cluster and an electrode on the semiconductor material.

FIGS. 11A and 11B depict an exemplary PAH system 1100 that include molecular absorbers 1108 attached to a wide gap 1104 semiconductor particle 1102 by interface layers 1106. The semiconductor particle 1102 is used for charge separation and not absorption and is comprised of a wide bandgap 1104 materials ($WO_3$, ZnO, $TiO_2$). In this example, the molecular absorbers 1108 absorb light and generate electrons or holes that are transferred to the semiconductor particle 1102. N-type wide gap semiconductors are used as electron acceptors and p-type wide gap semiconductors for hole acceptors. The hole or electron remaining within the molecular absorber is transferred to the reactants in solution by way of transfer moieties which are part of the molecular absorber 1108. The electrons discharged at cathode sites 1110 drive the reduction half reaction of hydrogen ions to hydrogen. Holes migrate to anode sites, which drive the oxidation half reaction. It is the molecular absorber, not the semiconductor particle 1102, which absorbs light energy and produces the electrical voltage potential across the semiconductor particle 1102. A protective layer 1112 protects the semiconductor particle 1102 during use.

In addition to the general descriptions of the embodiments of the present invention mentioned above, a list of examples is provided to illustrate in detail some of the embodiments of the present invention. It should be respected by those proficient in the art that the above discussion and the techniques disclosed in the following systems, along with processes which follow the techniques discovered by the inventors, should be considered as exemplary prototypes and can be made by making many or slight changes in the disclosed embodiments to obtain alike or parallel results without deviating much from the essence and scope of the invention. The first three examples discuss methods of forming a photoelectrosynthetically active heterostructures. The fourth example relates to one of the possible reactor systems that can be used for a solar energy conversion system. The fifth example relates to methods for reducing the rate of backreaction using protective coatings or complexing agents.

Example 1

An Exemplary Stable Artificial Photoelectrosynthetic (PS) Device for Production of Fuels and Chemicals The basic element of an artificial photosynthetic system is an independent photoelectrosynthetically active heterostructure (PAH) consisting of semiconductor absorber material protected by a transparent functional coating material with exposed cathode and anode electrocatalyst contacts. In general, processes for fabricating a stable artificial photoelectrosynthetic (PS) system comprise the steps: i) developing a high efficiency semiconductor light absorbers with band gaps matched to maximize solar spectrum absorbance, ii) developing an inorganic material stabilizing the semiconductor in the electrolyte media, thus allowing the use of less expensive and earth abundant semiconductor materials, iii) developing specific electrocatalysts for maximum efficiency formation of electrocatalytic products, and iv) developing a semi-selective electrocatalyst coating to allow use of homogeneous slurry reactors.

In one embodiment, the artificial photosynthetic device will consist of a transparent enclosed slurry reactor with suspended PAHs. The PAH consists of a light absorbing semiconductor junction polarized by a cathode electrocatalyst and an anode electrocatalyst with the semiconductor protected by a non-corrosive insulating layer (See FIG. 7A-7B). One or both of the electrocatalysts will have a semipermeable coating to prevent any back reactions (e.g. chromium oxide which will allow $H^+$ and $H_2$ but not organics to the cathode). Under illumination, the PAHs act as light harvesting antennae absorbing sunlight and producing usable charges which are then driven to the external contacts to carry out the necessary redox reactions producing valuable fuels and chemicals (See FIGS. 8A-8D). In one embodiment, the coating material as described in U.S. Provisional Application No. Application No. 61/559,717, filed Nov. 14, 2011, the disclosure of which is incorporated herein by reference, can be any conducting polymer which is optically transparent, electrically conducting, electrocatalytically active, energetically forming a type-II band offset with an underlying semiconductor layer, and stable in acidic and basic electrolytes. In such embodiments, coating materials include, but are not limited to, Poly (3, 4-ethylenedioxythiophene) (PEDOT) in natural and doped form, Poly (4, 4-dioctylcyclopentadithiophene) in natural and doped form, metallic carbon nanotubes (CNTs), or combinations thereof. The dopants for PEDOT include, but are not limited to, polystyrene sulfonate (PSS), tetra methacrylate (TMA), or combinations thereof. The dopants for poly (4, 4-dioctylcyclopentadithiophene) include, but are not limited to, iodine, 2, 3-dichloro-5, 6-dicyano-1, 4-benzoquinone (DDQ), and combinations thereof.

More specifically, in some embodiments, processes for developing stable artificial PS device comprise the steps: a) selecting/fabricating a high quality semiconductor such as silicon, gallium arsenide, indium phosphide, cadmium selenide, cadmium telluride, copper zinc tin sulfide, copper sulfide, tin sulfide, iron sulfide etc.; b) dispersing the coating material in a mixture of aqueous/non-aqueous solvent and homogenizing them; c) disposing the coating material on top of the absorber layer; d) annealing the coating to form a Schottky contact or to form an efficient hole transport layer depending upon the choice and design of the underlying semiconductor layer; d) positioning of electrocatalyst on the back of the absorber layer followed by annealing to form an Ohmic contact; e) mechanical breaking of the entire unit using ball mill, dicing saw or by laser cutting to obtain individual micron size PS units; and f) suspending the unit in a electrolyte (See FIGS. 9A-9C). In one example, the light absorption occurs in the p-n GaAs photovoltaic structure. The wireless PS cell was fabricated by e-beam depositing platinum at the cathode side (n-side) and spin casting PEDOT: PSS on the anode side (p-side) of GaAs wafer and was suspended in fuming hydrobromic acid (HBr) for production of $H_2$ and $Br_2$. PEDOT: PSS served as both transparent conducting hole transport layer and as an electrocatalyst for bromine evolution. Upon illumination, clear visual observation of $H_2$ bubbles on the cathode and bromine evolution at the anode was obtained. With no PEDOT: PSS coating, the cells failed immediately in HBr. The stability of the artificial photosynthetic unit was assessed by measuring the hydrogen production using a gas chromatograph (GC) column in a closed cell configuration. The cell was stable for 6 hours of continuous operation.

In another embodiment of the present invention the above PAH unit was used for oxidation of organic wastes to produce clean water and $H_2$.

In another embodiment of the present invention the above PAH unit was used for direct water splitting to produce $O_2$ and $H_2$ In another embodiment the above PAH unit was used for oxidation of formic acid to produce $CO_2$ and $H_2$ In another embodiment of the present invention, the oxidation and reduction electrocatalysts were loaded using photochemical processes. For example, gallium arsenide wafer can be first used to photoreduce (using chloroplatinic acid) Pt onto positions where electrons will transport, with the counter reaction being a facile non-metal deposition step (such as methanol oxidation), then in a separate solution such as nickel acetate and a sacrificial electron acceptor expose the solution to light to form an anode, such as NiOOH through an oxidation reaction, so that the Pt has been deposited where electrons transport and the NiOOH (which when oxidized will form NiO) will be deposited where the holes will transport.

Example 2

An Exemplary Stable Artificial Photoelectrosynthetic (PS) Device Based on Porous Anodic Aluminum Oxide (AAO) Membrane for Production of Fuels and Chemicals This example serves to exemplify the demonstration of fuel and chemical production in a device structure based on a porous AAO with low band gap semiconductor materials deposited within the pores and capped with anode and cathode electrocatalysts. One or both of the electrocatalysts will have a semi permeable coating to prevent any back reactions (e.g. chromium oxide which will allow $H^+$ and $H_2$ but not organics to the cathode).

The porous AAO serves as a protective membrane to solve the issue of instability of low band gap semiconductors when dipped in common electrolytes. Anode and cathode electrocatalysts, such as transition metals, caps the top and bottom of the semiconductor so as to separate the semiconductors from the electrolyte, reducing the chance of corrosion. An additional functional coating on the cathode will allow diffusion of protons and hydrogen but block the oxidation products from reacting and thus increase the Faradaic efficiency for production of hydrogen.

Figure 16A:
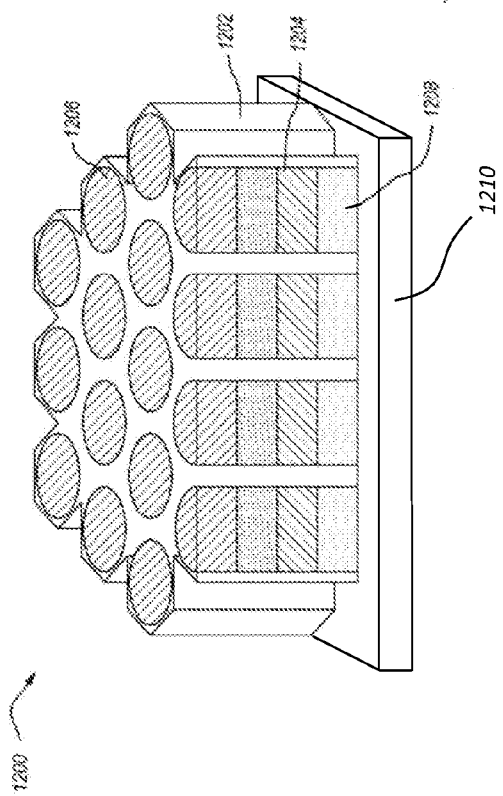
FIGS. 16A and 16B illustrate an artificial photoelectrosynthetic device having a honeycomb structure and housing isolated and autonomous light absorbing units, which each have isolated anodes and isolated cathodes.
Figure 16B:
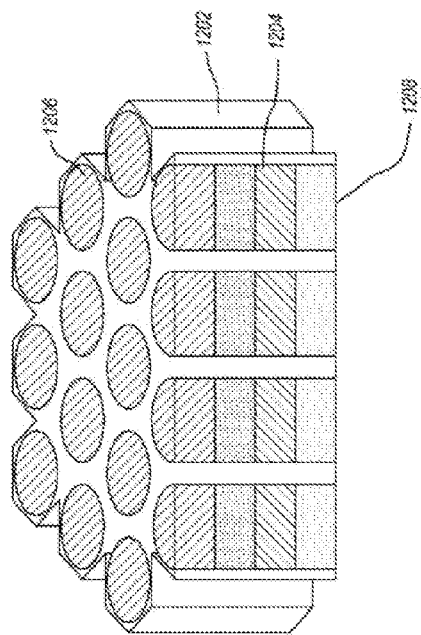

The process begins by creating a uniform array of elongated semiconductor absorber materials in the range 50-1000 nm in length and with diameters ranging from 20-200 nm by electrodeposition inside a properly fabricated porous anodic aluminum oxide (AAO) template. Porous AAO template is fabricated my methods as reported by us and elsewhere (step 1). The process begins by electropolishing aluminum foil in 1:5 mixtures of perchloric acid and ethanol at 20V in 5° C. The electropolished aluminum foil is then electrochemically anodized in 0.3 M oxalic acid or sulfuric acid. The anodizing voltages ranges from 20 V to 120 V depending on the required pore diameter and pore density. The pores may be further widened to desired diameter as reported elsewhere. The anodized aluminum oxide is then removed from the aluminum underlayer and the remaining alumina barrier layer is removed by wet or dry etching step (step 2). A thin metallic film is physical vapor deposited on one of the sides of porous AAO layer to form an electrically conducting backing layer (step 3). The material selected for the backing layer is chosen such a way that it can be mechanically or chemically etched later on. In step 4, one deposits the necessary PV device with appropriate electrocatalysts into the pores using electrodeposition or vapor-based deposition techniques (chemical vapor deposition, atomic layer deposition, etc.) followed by removal of the backing metallic film (step 5). For example, FIGS. 16A and 16B illustrate such a device 1200 showing a honeycomb-shaped protective structure 1202 housing isolated and autonomous light absorbing units 1204, which each have isolated anodes 1206 and isolated cathodes 1208. FIG. 16A illustrates the device 1200 with the electrically conducting backing layer 1210 (as described in step 3 above), and FIG. 16B illustrates the device 1200 after removal of the electrically conducting backing layer 1210 (as described in step 5 above). In one embodiment the absorber materials include low band gap materials such as CdTe, Si, GaAs, InP and metal sulfides CdS, $Cu_2S$, SnS, $Cu_2ZnSnS_4$, etc. To form an electric field for charge separation, diode junctions (such as CdS/CdTe), or Schottky junctions (such as CdSe/PEDOT:PSS) are fabricated inside the pores. The result is a dense array of nanometer sized PAHs separated from each other by a transparent protecting alumina membrane, and each unit within the pores serving as an autonomous solar fuel production unit maximizing the fault tolerance.

In one embodiment, a hybrid CdSe-PEDOT nanowire based PAH unit is fabricated with CdSe as the light absorber and PEDOT: PSS as the hole filter and oxidation catalyst. Each nanowire PAH unit consists of an n-CdSe light absorbing layer connected in series to a platinum electrocatalyst through a nickel-gold Ohmic contact segment. The other end of the CdSe is connected to PEDOT which functions both as a hole transporting Schottky contact layer and also as the anode electrocatalyst. The PAH unit was suspended in acidified HI solution. Upon illumination, holes flow towards the Schottky contact producing $I_2$ and electron flows toward the Ohmic contact to produce $H_2$. Only the cathode (Pt) and anode (PEDOT) electrocatalysts is exposed to the solution and CdSe is protected by the AAO.

In one embodiment of the present invention, a hybrid CdSe-PEDOT nanowire based PAH unit was used for formic acid oxidation to produce $CO_2$ and $H_2$.

In another embodiment of the present invention, a hybrid CdSe-PEDOT nanowire based PAH unit was used for methanol oxidation.

In another embodiment of the present invention, Cu/Cu2O/Au Schottky barrier solar cell was fabricated inside PAO for formic acid oxidation studies.

Example 3

Photoelectrochemically Active Heterostructures Using Silicon as the Photoabsorber In another embodiment of the invention silicon coated with PEDOT to form a Schottky junction was used as a photoelectrosynthetically active heterostructure to produce $H_2$ with the counter reactor the oxidation of vanadia ions.

Figure 12A:
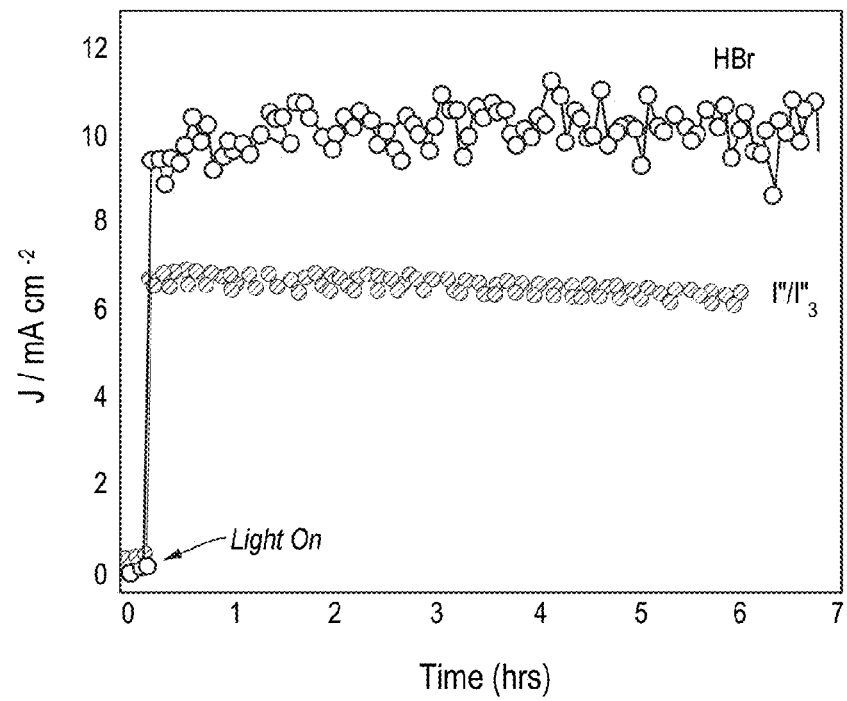
FIGS. 12A and 12B show a set of plots that illustrates the success of using a protective coating to protect the semiconductor from the electrolyte.
Figure 12B:
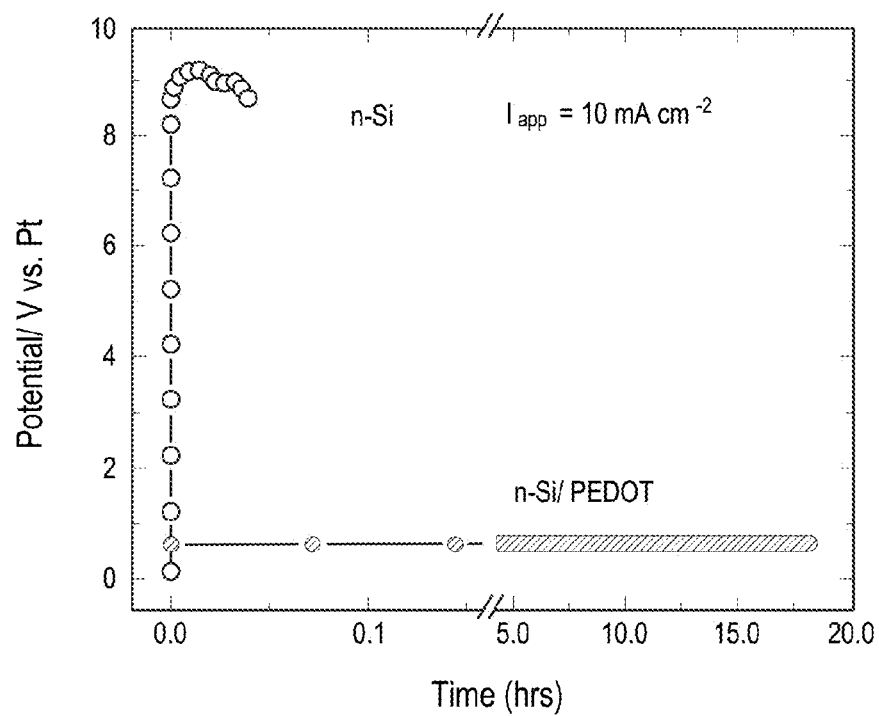

In another embodiment the silicon coated with PEDOT to form a Schottky junction was used to produce $H_2$ and $I_2$, as shown in FIGS. 12A-12B.

In another embodiment of the present invention the device described above could be used for the production of $H_2$ and the oxidation of methanol.

Example 4

Photoelectrochemical Reactor System for Production of Hydrogen

An embodiment of the present invention consists of a reactor that contains electrolyte, is permeable to sunlight, and is impermeable to the products, with a method of extraction for the products without destruction of the bag or need of removal of the electrolyte, and that contains the photoelectrochemically active heterostructures immersed and suspended in the electrolyte.

The reactor may consist of any plastic that is impermeable to the electrolyte and the gases (for example hydrogen and oxygen) such as a Food Saver baggie where the ends are sealed using a heat sealing method, or a Tedlar gas bag that has been sealed.

Figure 13A:
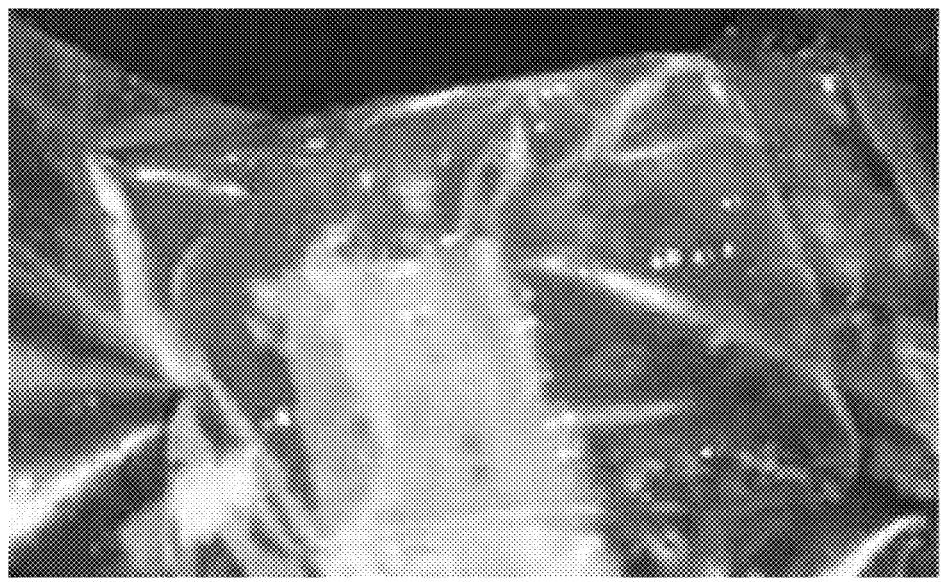
FIGS. 13A and 13B illustrate the use of a protective coating to avoid the reduction of light transmission that comes from the formation of water condensation on the reactor surface.
Figure 13B:
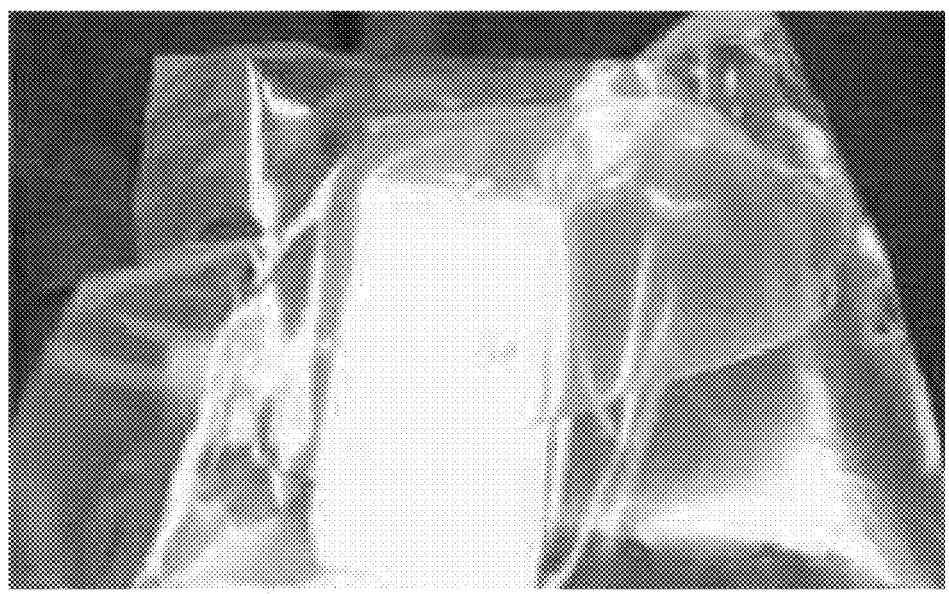

In order to maintain permeability to sunlight, the plastic material can be selected that will maintain permeability to light over time, as well as defogging agents that can be placed on the reactor to stop condensation of water vapor on the baggie surface, which can block the permeability of light into the reactor system. One example of avoiding this issue is using an anti-fogging material such as Rain-X in order to avoid the condensation of water that stops light from penetrating the baggie, shown in FIGS. 13A and 13B.

Figure 14:
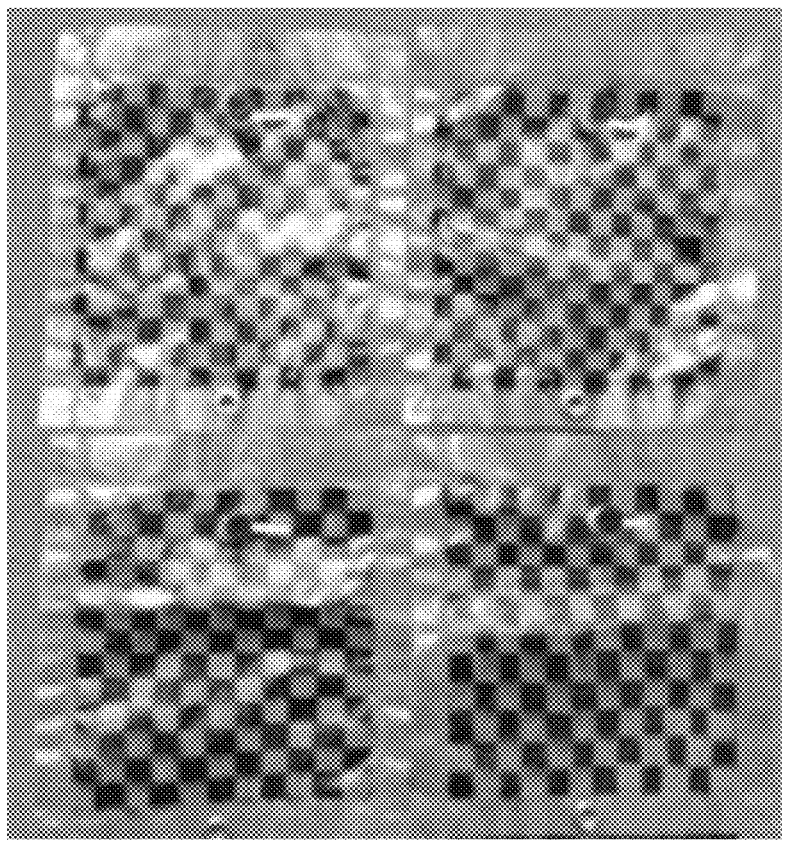
FIG. 14 illustrates a checkerboard pattern of the reactors that can be used to mix the electrolyte.

In order to suspend the PAH in the electrolyte, natural convection due to temperature gradients can be used to circulate the electrolyte. One method of using this is a checkerboard black/white pattern on the bottom of the baggie so that light that is not absorbed by the PAH structures may be preferentially absorbed on the black portions of the bottom of the baggie, causing differential heating between the black and white portions of the pattern, which can lead to natural convection and a mixing of the solution without need of an external stirring source. An example of such a pattern is shown in FIG. 14.

The gas that is formed in the headspace of the baggie can be collected through an opening in the same manner as a gas-bag that is commercially available, and brought to any location where the $H_2$ is required, such as a fuel cell.

Example 5

Figure 15A:
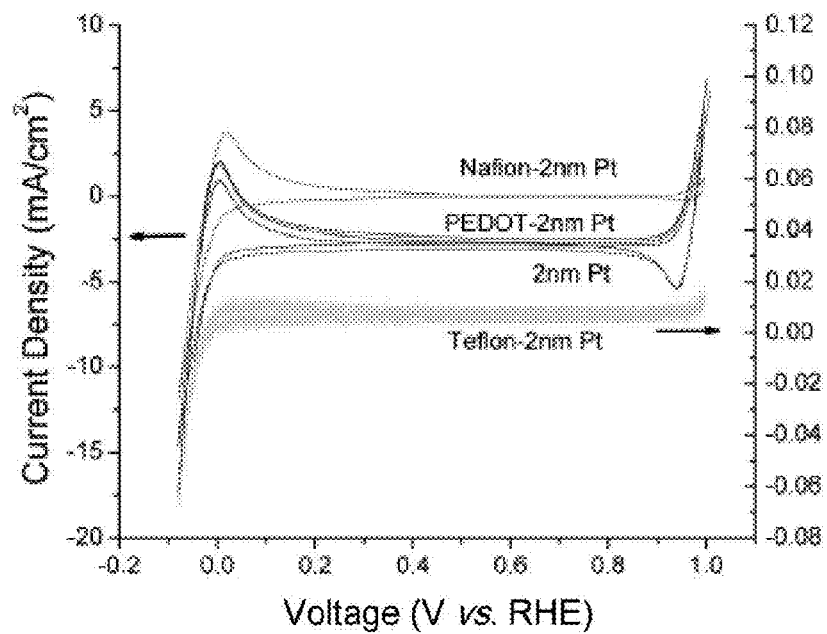
FIG. 15A is a plot that illustrates the effect of using a Nafion coating to prevent the unfavorable bromine back reaction.

Reducing the Rate of Backreaction in Photoelectrosynthetic Solar Energy Conversion In one embodiment of the invention the backreaction may be prevented through the use of a protective coating layer. The protective coating layer may consist of, but is not limited to, $Cr_2O_3$, or a polymer that preferentially allows H+ to pass through while blocking the ability of the oxidation product (ex. $Br_2/Br_3^-$) to pass through. An example of such a protective coating is a thin coating of Nafion, which is an excellent membrane for blocking bromine to prevent the parasitic backreaction of bromine reduction, which reduces the faradaic efficiency of hydrogen production, during photoelectrochemical electrolysis of HBr. Nafion preferentially allows $H^+$ to pass through, while minimizing the amount of bromine that can pass through. A comparison of the effect of Nafion in reducing the bromine oxidation (seen by the reduction current at higher potentials than the electrochemical reduction of water) compared to an uncoated and PEDOT coated electrode as well as a Teflon coated Pt electrocatalyst is shown in FIG. 15A. In addition to the effect of the reduction in backreaction, and increase in Faradaic efficiency of the production of products, the Nafion also serves to protect the hydrogen electrocatalyst from the presence of corrosive species such as bromine or bromide, which may otherwise poison or corrode the platinum electrocatalyst.

Figure 15B:
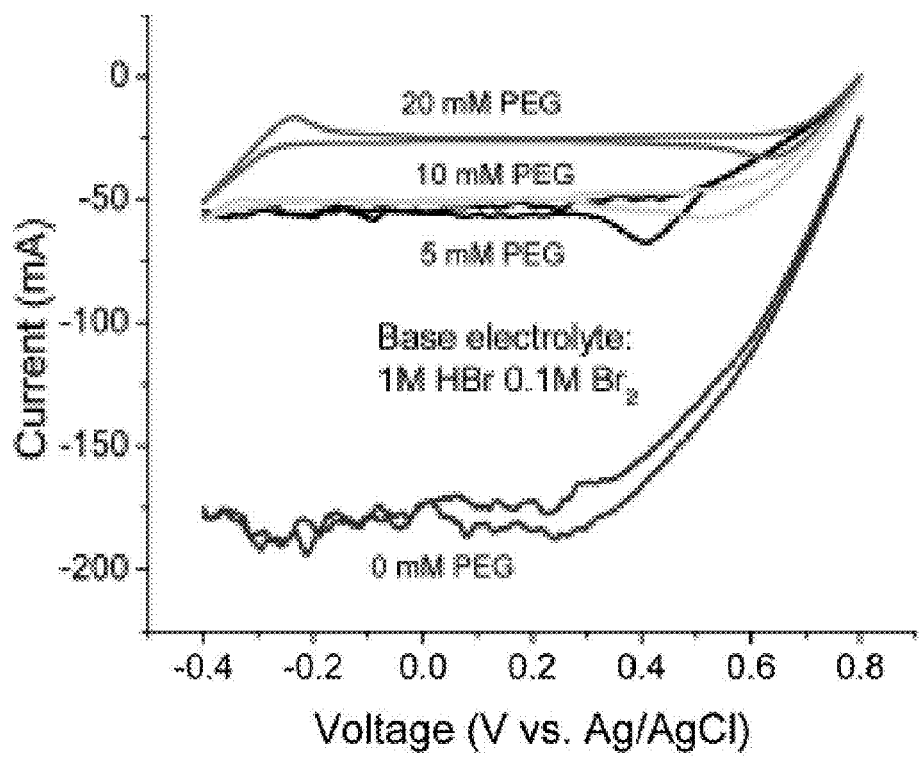
FIG. 15B is a plot that illustrates the use of polyethylene glycol to complex bromine and reduce the rate of bromine back reaction.

In another embodiment of the invention, the backreaction may be prevented by the complexation of the products to decrease their effective concentration in the solution. Polyethylene glycol can be used to complex bromine and reduce the backreaction of bromine reduction, as shown in FIG. 15B.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing a photoelectrosynthetically active heterostructure, comprising:
    forming or providing a plurality of nanosized cavities in an electrically insulating material;
    forming or providing a layer of an electrically conductive metal on one side of the electrically insulating material;
    depositing an electrocatalyst cathode layer in the plurality of cavities to form a plurality of cathodes;
    depositing one or more layers of light-absorbing semiconductor material in the plurality of cavities;
    depositing an electrocatalyst anode layer in the plurality of cavities to form a plurality of anodes;
    removing the layer of electrically conductive metal; and
    forming a hydrogen permeable layer over the electrocatalyst cathode layer,
    wherein the plurality of nanosized cavities are spaced so as to form a plurality of independent light absorbing units, and
    wherein the electrocatalyst anode layer is coupled to the independent light absorbing units and is isolated from the electrocatalyst cathode layer so that each independent light absorbing unit is autonomous from other light absorbing units.

2. The method of claim 1, wherein the one or more layers of light-absorbing semiconductor material comprise one or more p-n junctions formed by one or more layers of p-type semiconductor material adjacent to one or more layers of n-type semiconductor material.

3. The method of claim 1, wherein the one or more layers of light-absorbing semiconductor material comprise one or more layers of p-type semiconductor material or n-type semiconductor material that form one or more Schottky junctions.

4. The method of claim 1, wherein the electrically insulating material is selected from the group consisting of $Al_2O_3$, $SiO_2$, ZrO, $AlF_3$, $TiF_2$, ZnO, $TiO_2$, metal oxides, and oxides of n-type or p-type semiconductor materials.

5. The method of claim 1, wherein forming or providing the one or more cavities within an electrically insulating material comprises forming a plurality of cavities within a metal foil and oxidizing metal surfaces within the cavities to form an electrically insulating metal oxide.

6. The method of claim 5, wherein the electrically insulating metal oxide is formed using at least one of dry etching or electrochemical anodization.

7. The method of claim 1, wherein the electrocatalyst cathode layer, the light-absorbing semiconductor material, and the electrocatalyst anode layer are deposited in the one or more cavities by one or more of electrodeposition, vapor deposition, chemical vapor deposition, or atomic layer vapor deposition.

8. The method of claim 1, wherein the layer of electrically conductive metal is removed by mechanical or chemical etching.

9. The method of claim 1, wherein the electrocatalyst cathode layer and/or the electrocatalyst anode layer are deposited in the one or more cavities prior to removing the layer of electrically conductive metal.

10. The method of claim 1, wherein the electrocatalyst cathode layer and/or the electrocatalyst anode layer are deposited in the one or more cavities after removing the layer of electrically conductive metal.

11. The method of claim 1, wherein the one or more layers of semiconductor material comprise at least one p-type semiconductor material selected from the group consisting of intrinsic or p-doped SnS, ZnS, CdS, CdSe, CdTe, $Cu_2S$, $WS_2$, $Cu_xO$, $Cu_2ZnSnS_4$, $CuIn_xGa_{1-x}Se_2$, GaN, InP, or SiC; doped (p-type) or undoped elemental Si or Ge; and doped (p-type) or undoped compound semiconductors selected from metal sulfides, selenides, arsenides, nitrides, antinomides, phosphides, oxides, tellurides, and mixtures containing, respectively, sulfur (S) selenium (Se), arsenic (As), antimony (Sb), nitrogen (N), oxygen (O) tellurium (Te), and/or phosphorus (P) as one or more electronegative element(s) A, and one or more metals (M), of the form $M_nA_x$ where M is one or a combination of elements selected from Cu, Ga, Ge, Si, Zn, Sn, W, In, Ni, Fe, Mo, Bi, Sb, or Mg.

12. The method of claim 1, wherein the one or more layers of semiconductor material comprise at least one n-type semiconductor material selected from the group consisting of intrinsic or n-doped InS, CdTe, CdS, CdSe, CdTe, $Cu_2S$, $WS_2$, $Cu_xO$, $Cu_2ZnSnS_4$, $CuIn_xGa_{1-x}Se_2$, GaN, InP, or SiC; doped (n-type) or undoped elemental Si or Ge; and doped (n-type) or undoped compound semiconductors selected from metal sulfides, selenides, arsenides, nitrides, antinomides, phosphides, oxides, tellurides, and their mixtures containing respectively, sulfur (S), selenium (Se), arsenic (As), antimony (Sb), nitrogen (N), oxygen (O), tellurium (Te), and/or phosphorus (P) as one or more electronegative element(s) (A), and one or more metals (M), of the form $M_nA_x$ where M is one or a combination of elements selected from Cu, Ga, Ge, Si, Zn, Sn, W, In, Ni, Fe, Mo, Bi, Sb, or Mg.

13. The method of claim 1, wherein the electrocatalyst cathode layer comprises at least one conductor material selected from the group consisting of platinum group metals, Pt, Au, transition metals, transition metal oxides, NiO, metal carbides, WC, metal sulfides, $MoS_2$, electrical conducting carbon containing materials, graphite, graphene, and carbon nanotubes.

14. The method of claim 1, wherein the electrocatalyst anode layer comprises at least one conductor material selected from the group consisting of metals, oxides and mixtures of metals selected from Ru, Ag, V, W, Fe, Ni, Pt, Pd, Ir, Cr, Mn, Cu, or Ti; metal sulfides; $MoS_2$; electrical conducting carbon containing materials; graphite; graphene; and carbon nanotubes.

15. The method of claim 1, wherein the hydrogen permeable layer comprises at least one material selected from the group consisting of chromium (III) oxide ($Cr_2O_3$), nafion membranes made from sulfonated tetrafluoroethylene-based fluoropolymer-copolymers, acrylics, mixtures of metal oxides, $WCrO_x$, and $WZrCeO_x$.

16. A method of manufacturing a photoelectrosynthetically active heterostructure, comprising:
    forming or providing a protective membrane comprising an electrically insulating sheet and a plurality of cavities in the electrically insulating sheet;
    forming or providing an electrically conductive metal layer on one side of the electrically insulating sheet;
    depositing by electrodeposition, vapor deposition, chemical vapor deposition, or atomic layer vapor deposition an electrocatalyst cathode layer in the plurality of cavities;
    depositing by electrodeposition, vapor deposition, chemical vapor deposition, or atomic layer vapor deposition one or more layers of light-absorbing semiconductor material in the plurality of cavities;
    depositing by electrodeposition, vapor deposition, chemical vapor deposition, or atomic layer vapor deposition an electrocatalyst anode layer in the plurality of cavities; and
    removing the electrically conductive metal layer from the electrically insulating sheet,
    wherein the plurality of nanosized cavities are spaced so as to form a plurality of independent light absorbing units, and
    wherein the electrocatalyst anode layer is coupled to the independent light absorbing units and is isolated from the electrocatalyst cathode layer so that each independent light absorbing unit is autonomous from other light absorbing units.

17. The method of claim 16, further comprising forming a hydrogen permeable layer over the electrocatalyst cathode layer.

18. A method of manufacturing a photoelectrosynthetically active heterostructure, comprising:
    forming or providing a protective membrane comprising anodized aluminum oxide and a plurality of nanosized pores in the protective membrane;
    forming or providing an electrically conductive metal layer on one side of the protective membrane;
    electrodepositing an electrocatalyst cathode material in the plurality of nanosized pores;
    electrodepositing one or more layers of light-absorbing semiconductor material in the plurality of nanosized pores;
    electrodepositing an electrocatalyst anode material in the plurality of nanosized pores; and
    removing the electrically conductive metal layer from the protective membrane,
    wherein the plurality of nanosized pores are arranged so as to provide a plurality of independent light absorbing units, and
    wherein the electrocatalyst anode material is coupled to the independent light absorbing units and is isolated from the electrocatalyst cathode material so that each independent light absorbing unit is autonomous from other light absorbing units.

* * * * *

UNITED STATES PATENT AND TRADEMARK OFFICE
CERTIFICATE OF CORRECTION

PATENT NO. : 9,935,234 B2
APPLICATION NO. : 15/418236
DATED : April 3, 2018
INVENTOR(S) : McFarland et al.

It is certified that error appears in the above-identified patent and that said Letters Patent is hereby corrected as shown below:

In the Specification

Column 1
Line 64, change "matrix 118" to —matrix 18—

Column 8
Line 49, change "produces" to —products—
Line 57, change "product" to —produce—

Column 9
Line 64, change "radiation 406" to —radiation 405—

Column 11
Line 38, change "314" to —414—
Line 46, change "314" to —414—

Column 12
Line 6, change "reaction 512a" to —reaction 510a—

Column 15
Line 66, change "combine" to —combined—

Column 16
Line 18, change "combine" to —combined—

Column 17
Line 42, change "surface" to —surfaces—

Signed and Sealed this
Sixteenth Day of October, 2018

Andrei Iancu
*Director of the United States Patent and Trademark Office*

CERTIFICATE OF CORRECTION (continued)
U.S. Pat. No. 9,935,234 B2

Column 18
Line 4, change "anodes/cathode" to —anode/cathode—
Line 36, change "designed have" to —designed to have—

Column 19
Line 51, remove [a]

Column 20
Line 27, change "device" to —devices—

Column 21
Line 31, change "caps" to —cap—
Line 43, change "my" to —by—
Line 48, change "ranges" to —range—
Line 57, change "chosen such" to —chosen in such—

Column 23
Line 29, remove [the]